United States Patent
Kakefuda et al.

(10) Patent No.: US 7,498,429 B2
(45) Date of Patent: Mar. 3, 2009

(54) AHAS SMALL SUBUNIT PROMOTER

(75) Inventors: Genichi Kakefuda, Princeton Junction, NJ (US); Colleen Costello, Lawrenceville, NJ (US); Ming Sun, Groveville, NJ (US); Weiming Hu, Dresher, PA (US)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 12/027,011

(22) Filed: Feb. 6, 2008

(65) Prior Publication Data

US 2008/0163398 A1    Jul. 3, 2008

Related U.S. Application Data

(60) Division of application No. 10/970,515, filed on Oct. 21, 2004, now Pat. No. 7,351,880, which is a division of application No. 09/997,900, filed on Nov. 30, 2001, now Pat. No. 6,825,399, which is a continuation of application No. 09/426,568, filed on Oct. 22, 1999, now Pat. No. 6,348,643.

(60) Provisional application No. 60/106,239, filed on Oct. 29, 1998.

(51) Int. Cl.
- C12N 15/11 (2006.01)
- C12N 15/82 (2006.01)
- A01H 5/00 (2006.01)
- A01H 5/10 (2006.01)

(52) U.S. Cl. .................. 536/24.1; 435/419; 435/320.1; 800/278; 800/295

(58) Field of Classification Search .............. None
See application file for complete search history.

(56) References Cited

U.S. PATENT DOCUMENTS

| | | |
|---|---|---|
| 5,013,659 A | 5/1991 | Bedbrook et al. |
| 5,141,870 A | 8/1992 | Bedbrook et al. |
| 5,304,732 A | 4/1994 | Anderson et al. |
| 5,378,824 A | 1/1995 | Bedbrook et al. |
| 5,539,092 A | 7/1996 | Haselkorn et al. |
| 5,597,717 A | 1/1997 | Guerineau et al. |
| 5,605,011 A | 2/1997 | Bedbrook et al. |
| 5,633,437 A | 5/1997 | Bernasconi et al. |
| 5,633,444 A | 5/1997 | Guerineau et al. |
| 5,643,779 A | 7/1997 | Ehrlich et al. |
| 5,719,046 A | 2/1998 | Guerineau et al. |

(Continued)

FOREIGN PATENT DOCUMENTS

EP        036750 A2   3/1990

(Continued)

OTHER PUBLICATIONS

GenBank Acession No. AC006533, NCBI, National LIbrary of Medicine USA, Bethesda, MD.*

(Continued)

*Primary Examiner*—David H Kruse
(74) *Attorney, Agent, or Firm*—Alston & Bird LLP

(57) ABSTRACT

A promoter sequence and plant expression vectors encoding for an eukaryotic AHAS small subunit protein are disclosed. The DNA sequences and vectors are used to transform plants to produce transgenic plants which possess elevated levels of tolerance or resistance to herbicides, such as imidazolinones.

8 Claims, 9 Drawing Sheets

U.S. PATENT DOCUMENTS 5,767,366 A 6/1998 Sathasivan et al.

FOREIGN PATENT DOCUMENTS

| JP | 8214852 A | 8/1996 |
| WO | WO 96/33270 A1 | 10/1996 |
| WO | WO 98/37206 A1 | 8/1998 |

OTHER PUBLICATIONS

Sequence Revision History for GenBank Accession No. AC006533, NCBI, National LIbrary of Medicine USA, Bethesda, MD.*

Duggleby, R., "Identification of an Acetolactate Synthase Small Subunit Gene in Two Eukaryotes," *Gene*, 1997, pp. 245-249, vol. 190.

EMBL Database Report for Accession No. AC006533, 1999 (XP-002136603).

Hershey, H., et al., "Cloning and Functional Expression of the Small Subunit of Acetolactate Synthase from *Nicotiana plumbaginifolia*," *Plant Molecular Biology*, 1999, pp. 795-806, vol. 40, Kluwer Academic Publishers, Netherlands.

Koziel, M., et al., "Optimizing Expression of Transgenes with an Emphasis on Post-Transcriptional Events," *Plant Molecular Biology*, 1996, pp. 393-405, vol. 32.

Miflin, B., "Cooperative Feedback Control of Barley Acetohydroxyacid Synthetase by Leucine, Isoleucine, and Valine," *Archives of Biochemistry and Biophysics*, 1971, pp. 542-550, vol. 146.

Weinstock, O., et al., "Properties of Subcloned Subunits of Bacterial Acetohydroxy Acid Synthases," *Journal of Bacteriology*, 1992, pp. 5560-5556, vol. 174, No. 17, American Society for Microbiology.

Response to First Written Opinion on Preliminary Examination for International Application No. PCT/US99/25452; dated Nov. 28, 2000.

* cited by examiner

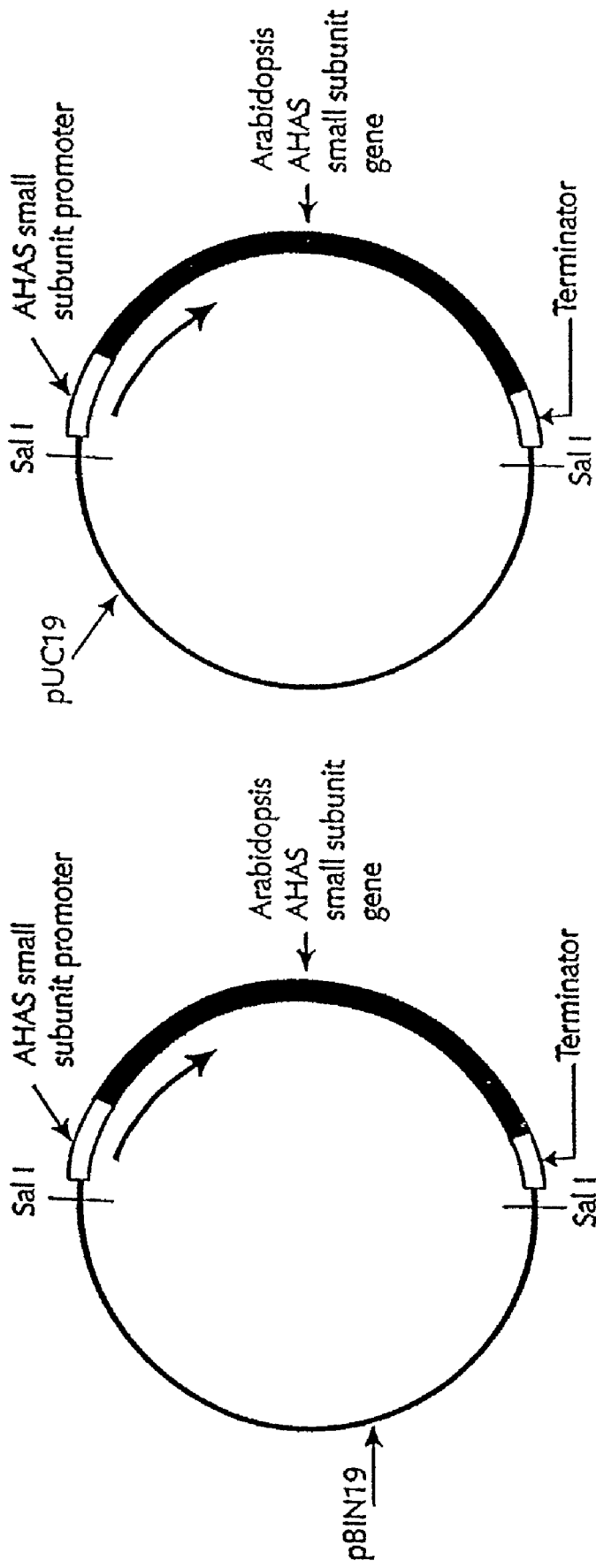

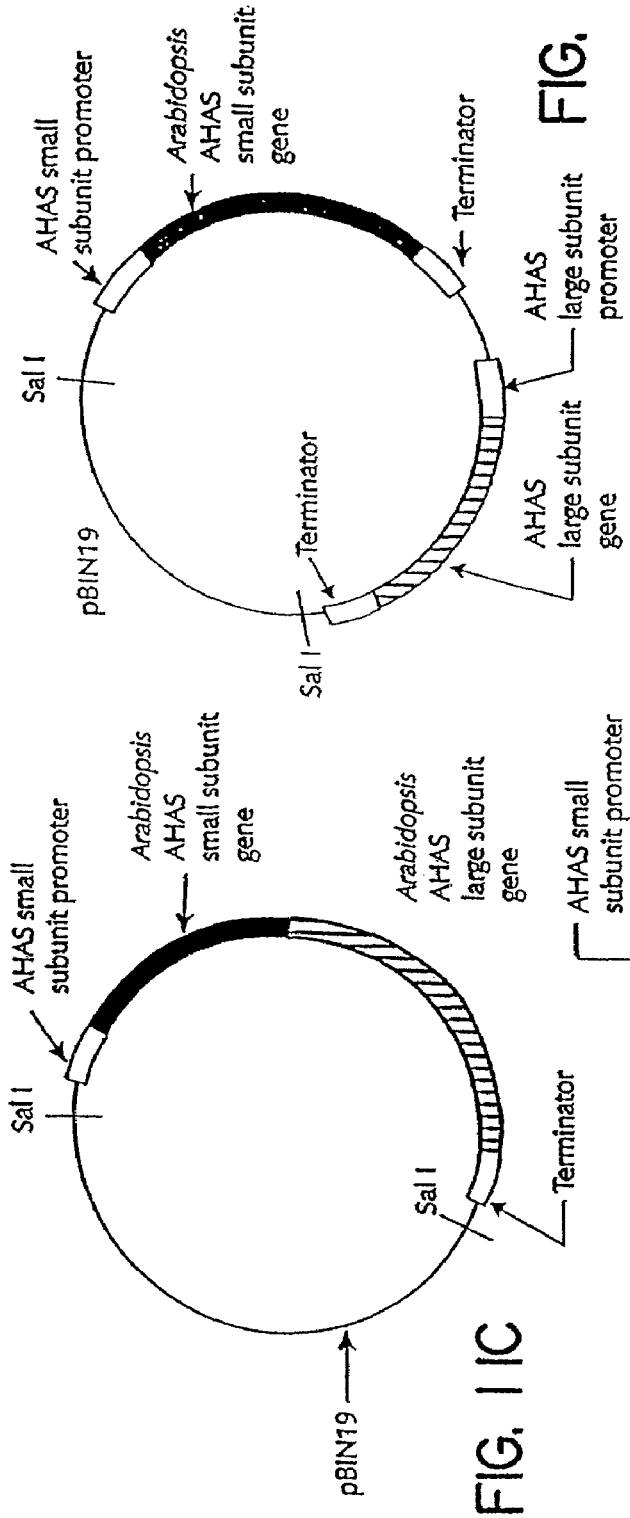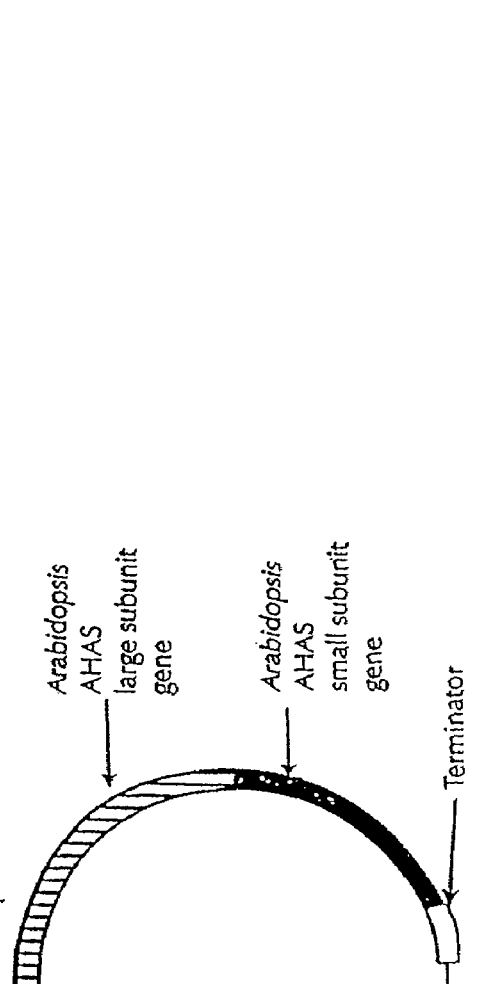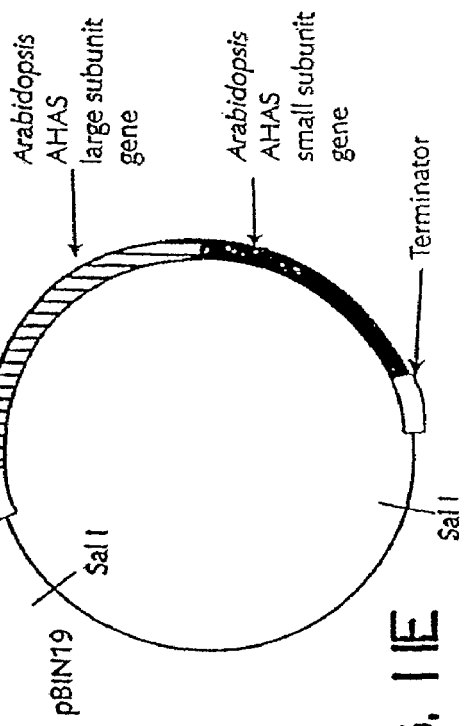
PLANT EXPRESSION VECTORS
FIG. 1C
FIG. 1D
FIG. 1E

AHAS SMALL SUBUNIT PROMOTER

CROSS REFERENCE TO RELATED APPLICATION

This application is a divisional of U.S. application Ser. No. 10/970,515, filed Oct. 21, 2004, which was a divisional of U.S. application Ser. No. 09/997,900, filed Nov. 30, 2001, now U.S. Pat. No. 6,825,399, which was a continuation of U.S. application Ser. No. 09/426,568, filed Oct. 22, 1999, now U.S. Pat. No. 6,348,643, which claims the benefit, under 35 U.S.C. 119(e), of U.S. Provisional Patent Application Ser. No. 60/106,239 filed Oct. 29, 1998; all of which are hereby incorporated herein by reference in their entirety.

BACKGROUND OF THE INVENTION

Herbicides are used extensively in agronomy for controlling weeds and other undesirable plants. Because of their phytotoxicity, herbicides also kill or significantly inhibit the growth and yield of desirable plants.

Some plants, for example *Arabidopsis*, inherently possess or develop resistance to certain herbicides upon repeated exposure to herbicides with the same mode of action. It has been a goal of plant biotechnologists to identify, isolate and clone plant genes that confer resistance to herbicides and use these genes to transform desirable plants such as crops to render them herbicide resistant.

Several methods for generating or identifying herbicide resistance in plants are known. For example, U.S. Pat. Nos. 5,719,046, 5,633,444 and 5,591,717 disclose a plant sulfonamide resistant gene and methods for transforming plant cells whose growth is inhibited by sulfonamides, with vectors containing this gene.

U.S. Pat. No. 5,405,765 discloses a method for producing transgenic wheat plants. This method comprises delivering a heterologous DNA to a Type C embryonic wheat callus in a suspension culture by an accelerated particle bombardment method.

U.S. Pat. No. 5,539,092 discloses polynucleotides encoding a cyanobacterial and plant acetyl-CoA carboxylase. This patent discloses processes for increasing the herbicide resistance of a monocotyledonous plant, comprising transforming the plant with a DNA molecule encoding a herbicide resistant polypeptide having the ability to catalyze the carboxylation of acetyl-CoA. The patent further discloses that the transgenic plants produced are resistant to herbicides such as arylphenoxyproprionates and cyclohexanediones.

U.S. Pat. No. 5,304,732 discloses methods for isolating herbicide-resistant plants. The patent describes the use of in vitro cell culture methods for isolating plant cell lines that are resistant to herbicides such as imidazolinones and sulfonamides.

The trait for a specific herbicide resistance is most often associated with a particular enzyme. One such enzyme which has been of interest in its association of conferring herbicide resistance in plants is acetohydroxy-acid synthase ("AHAS"), also known as acetolactate synthase ("ALS," E.C. 4.1.3.18). It is an essential enzyme in plants and many microorganisms, and in most plants the enzyme is sensitive to herbicides. The AHAS enzyme catalyzes the first step in the biosynthesis of the branched-chain amino acids, isoleucine, leucine, and valine, and its activity is allosterically inhibited by these amino acids. AHAS activity is also inhibited by several classes of herbicides, including imidazolinone compounds such as imazethapyr (PURSUIT®, American Cyanamid, Parsipanny, N.J.); sulfonylurea-based compounds such as sufometuron methyl (OUST®, E.I. du Pont de Nemours and Company, Wilmington, Del.); triazolopyrimidine sulfonamides (Broadstrike™, Dow Elanco; see Gerwick et al. *Pestic. Sci.* 29: 357-364, 1990); sulfamoylureas (Rodaway et al., *Mechanism of Selectively of Ac* 322,140 *in Paddy Rice, Wheat and Barley*, Proc. Brighton Crop Protec. Conf., Weeds, 1993); pyrimidyl-oxy-benzoic acids (STABLE®, Kumiai Chemical Industry Co., E.I. du Pont de Nemours and Company), and sulfonylcarboxamides (Alvarado et al., U.S. Pat. No. 4,883,914). Inhibition of AHAS activity may lead to the inability of the plant to make the branched amino acids or to the accumulation of toxic metabolites and, therefore, plant death.

Genes encoding AHAS enzymes have been isolated from enteric bacteria, including *Escherichia coli*, and *Salmonella typhimurium*. U.S. Pat. No. 5,643,779 discloses a nucleic acid sequence coding for an α-AHAS enzyme from *Lactococcus* and vectors containing same for transforming microorganisms. The transgenic microorganisms produce an enhanced amount of the AHAS enzyme.

Japanese Patent Document No. JP08214882 discloses a nucleic acid sequence for a large and a small subunit of AHAS from *Rhodobacter capsulatus*. The gene sequences are used to transform photosynthetic microorganisms to improve the production of AHAS enzyme for the synthesis of amino acids.

In eukaryotes, a gene encoding a polypeptide homologous to the large subunits of bacterial AHAS enzymes has been identified in the yeast *Saccharomyces cerevisiae*. Genes encoding mutant large subunits of AHAS from various plants have also been isolated, cloned, and used to create transgenic plants that are resistant to herbicides.

U.S. Pat. Nos. 5,605,011, 5,013,659, 5,141,870 and 5,378,824 disclose nucleic acid fragments encoding a mutant plant ALS protein associated with herbicide resistance. The mutant ALS large subunit protein confers herbicide resistance to sulfonylurea compounds in plants. The nucleic acid fragments encoding this mutant large subunit protein are used in vectors to transform plants which are normally sensitive to sulfonylurea herbicides. The transgenic plants resulting from such transformation are resistant to sulfonylurea herbicides.

U.S. Pat. No. 5,633,437 discloses a large subunit gene and enzyme isolated from cocklebur, *Xanthium* sp., which confer resistance to several structurally unrelated classes of herbicides in plants, plant tissues and seeds. The patent discloses herbicides which normally inhibit AHAS activity.

Herbicide resistant AHAS large subunit genes have also been rationally designed. WO 96/33270, U.S. Pat. Nos. 5,853,973 and 5,928,937 disclose structure-based modeling methods for the preparation of AHAS variants, including those that exhibit selectively increased resistance to herbicides such as imidazolines and AHAS inhibiting herbicides. This document discloses isolated DNAs encoding such variants, vectors containing these DNAs, methods for producing the variant polypeptides, and herbicide resistant plants containing specific AHAS gene mutations.

The prokaryotic AHAS enzymes exist as two distinct, but physically associated, protein subunits. In prokaryotes, the two polypeptides, a "large subunit" and a "small subunit," are expressed from separate genes. Three major AHAS enzymes, designated I, II and III, all having large and small subunits, have been identified in enteric bacteria. In prokaryotes, the AHAS enzyme has been shown to be a regulatory enzyme in the branched amino acid biosynthetic pathway (Miflin, B. J. *Arch. Biochm. Biophys.* 146:542-550, 1971), and only the large subunit has been observed as having catalytic activity. From studies of AHAS enzymes from microbial systems, two roles have been described for the small subunit: 1) the small subunit is involved in the allosteric feedback inhibition of the catalytic large subunit when in the presence of isoleucine, leucine or valine or combinations thereof; and 2) the small subunit enhances the activity of the large subunit in the absence of isoleucine, leucine or valine. The small subunit has also been shown to increase the stability of the active conformation of the large subunit (Weinstock et al. *J. Bacteriol.* 174:5560-5566, 1992). The expression of the small subunit can also increase the expression of the large subunit as seen for AHAS I from *E. coli* (Weinstock et al. *J. Bacteriol.* 174: 5560-5566, 1992).

In these microbial systems, the large subunit alone in vitro exhibits a basal level of activity that cannot be feedback-inhibited by the amino acids isoleucine, leucine or valine. When the small subunit is added to the same reaction mixture containing the large subunit, the specific activity of the large subunit increases.

The large AHAS subunit protein has been identified in plants and isolated and used to transform plants. An AHAS mutant allele isotype of the AHAS3 large subunit protein, having the tryptophan at position 557 replaced with leucine has been found in a *Brassica napus* cell line (Hattori et al. *Mol. & Gen. Genet.* 246: 419-425, 1995). The mutant protein product of this gene confers sulfonylurea, imidazolinone and triazolopyridine resistance to the cell line. This mutant allele, when expressed in transgenic plants, also confers resistance to these herbicides.

An AHAS herbicide-resistant, double-mutant allele of the large subunit of *Arabidopsis thaliana* has also been identified (*Planta* 196:64-68, 1995). The gene, csr1-4, encodes an AHAS enzyme with altered kinetics which is resistant to chlorsulfuron, imazapyr, and triazolopyrimidine. The csr1-4 gene when expressed in plants affects the growth of the plants in response to added L-valine and L-leucine.

Until recently, there was no direct evidence that a small subunit protein of AHAS existed in eukaryotic organisms. Recently, other groups, through the use of Expressed Sequence Tags (ESTs), have identified sequences homologous to the microbial AHAS small subunit genes in a eukaryote, the plant *Arabidopsis*. They showed that a randomly isolated *Arabidopsis* cDNA sequence had sequence homology with AHAS small subunit sequences from microbial systems. Since then, ESTs from small subunit genes have been described from other eukaryotes such as yeast and red algae (Duggleby 1997, *Gene* 190:245). Duggleby discloses three EST sequences, two from *Arabidopsis* and one from rice, that have homology to known prokaryotic small subunit gene sequences.

More recently, WO 98/37206 discloses the use of an ALS small subunit cDNA sequence from *Nicotiana plumbaginifolia* for screening herbicides which inhibit the holoenzyme. Until the present invention, however, the complete genomic sequence of a eukaryotic AHAS small subunit protein gene had not been determined, nor had a eukaryotic AHAS small subunit protein been produced or isolated from *Arabidopsis*.

SUMMARY OF THE INVENTION

The present invention provides DNA sequences encoding a biologically functional eukaryotic AHAS small subunit protein and functional variants thereof. In accordance with the invention, the *Arabidopsis* AHAS small subunit gene has been cloned and sequenced. Expression vectors containing DNA sequences encoding a eukaryotic AHAS small subunit protein are provided for transforming plants. Expression vectors are also provided which contain genes encoding both large and small subunits of an AHAS protein or proteins. The vectors may be used in methods to produce transgenic plants of interest, such as dicot and monocot crop-plants, including wheat, barley, rice, sugarcane, cotton, corn, soybean, sugar beet, canola and the like. The transgenic plants so produced will possess an elevated level of tolerance to certain herbicides, such as imidazolinones.

The invention also relates to methods for constructing DNA vectors including plasmids containing the AHAS small subunit protein genes. The vectors of the invention are suitable for transforming a broad range of plants and may also be engineered to contain a DNA sequence encoding an AHAS large subunit protein.

Vectors containing the complementary eukaryotic small subunit protein gene, for example, the gene derived from *Arabidopsis* or maize, can be used to transform an imidazolinone-tolerant plant to enhance herbicide resistance by a secondary mechanism.

In a specific embodiment of the invention, expression vectors are provided which contain DNA sequences encoding the large and small AHAS subunit proteins and the promoters for the large and small subunits of AHAS as coordinately regulated expression systems in plants.

For certain monocot crops, it may be preferred to use a monocot AHAS small subunit gene and promoter such as those derived from rice or maize. These genes are useful for applications involving the development of transgenic monocot plants which exhibit herbicide resistance to imidazolinones or other AHAS-inhibiting herbicides.

In one embodiment, the invention relates to a method for creating transgenic crop plants that exhibit high-level tolerance or resistance to imidazolinone herbicides. The method comprises introducing a DNA construct, such as a plasmid vector containing an herbicide resistant mutant of the AHAS large subunit gene and an AHAS small subunit gene, into a plant that is normally sensitive or partially resistant to imidazolinones. Once the vector is introduced into plant tissue, the vector uses the endogenous mechanisms of the plant to express the large and small subunit proteins. The increased production of exogenous large and small subunits of the AHAS enzyme confers enhanced imidazolinone resistance to the plant. This increased imidazolinone resistance results from an increase in catalytic activity, stability, resistance to degradation or resistance to inhibition of the large subunit protein in the presence of increased amounts of small subunit protein in the plant.

In a preferred embodiment, the large and small subunit genes of the AHAS enzyme are present on a single plasmid which integrates as one into the genome of the transformed plants, and segregates as a single locus for easier breeding of herbicide resistant crops.

In another embodiment of the invention, the DNA construct or vector comprises a herbicide-resistant large AHAS subunit gene and a small AHAS subunit protein gene fused into a single gene, operably linked to and expressed from a single promoter.

The small subunit protein of AHAS produced by the present vectors may also be used as a new target site for herbicides or used in combination with the large subunit to screen for putative inhibitors of the large subunit.

The invention also relates to methods of utilizing the small subunit DNA sequences as screening tools to identify mutations of the AHAS enzyme which confer herbicide resistance in plants. In this aspect of the invention, organisms coexpressing the large and small subunit of AHAS are screened for mutations which confer resistance to herbicides in plants. The mutant gene products are isolated and tested in vivo for the effects of herbicides including imidazolinones. Then, mutant herbicide resistant forms are isolated.

BRIEF DESCRIPTION OF THE DRAWINGS

FIG. 11A-11E illustrate the plant transformation (expression) vectors of the invention.

DETAILED DESCRIPTION OF THE INVENTION

Figure 1:
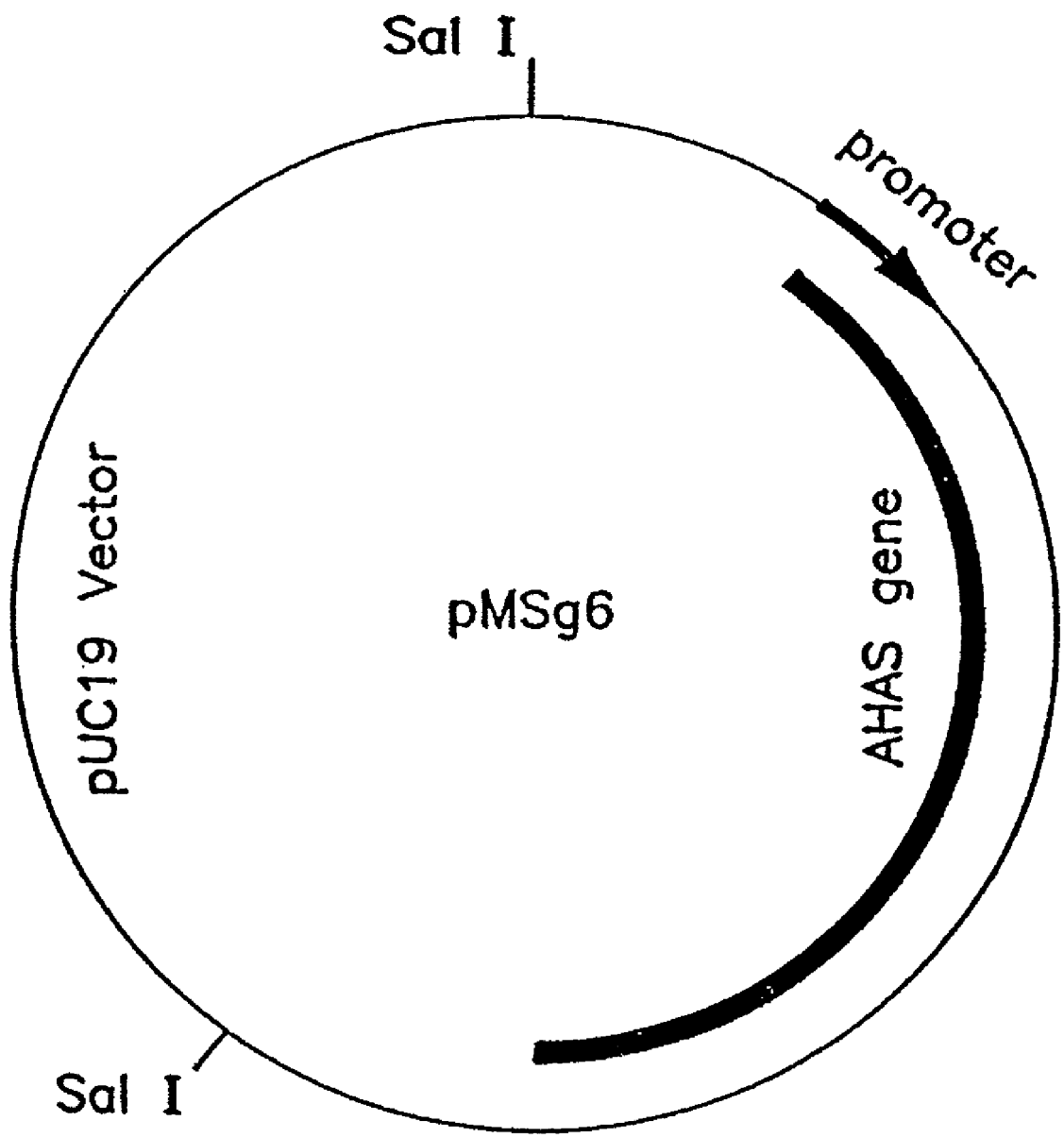
FIG. 1 depicts the pUC19 plasmid plant expression vector construct containing an *Arabidopsis* AHAS small subunit genomic DNA sequences of the invention.

The present invention relates to the cloning and sequencing of an AHAS small subunit protein gene of *Arabidopsis*. SEQ ID NO:1 in the Sequence Listing contains the nucleotide sequence of the *Arabidopsis* AHAS small subunit cDNA. The corresponding amino acid sequence of the encoded AHAS small subunit polypeptide is shown in SEQ ID NO:2 in the Sequence Listing. The genomic DNA sequence of the *Arabidopsis* AHAS small subunit gene is shown in SEQ ID NO:3 of the Sequence Listing.

The invention also relates to an isolated DNA sequence encoding a eukaryotic acetohydroxy-acid synthase, AHAS small subunit protein. Specifically, the invention relates to a DNA sequence which encodes a plant AHAS small subunit protein, which can be obtained from a dicotyledonous plant such as *Arabidopsis*, or a monocotyledonous plant such as rice or maize.

The cloned *Arabidopsis* AHAS small subunit gene sequences can be used in DNA vector constructs to transform crop plants which are normally-sensitive or partially resistant to herbicides such as imidazolinone. The transgenic plants obtained following transformation show increased resistance to AHAS-inhibiting herbicides such as imidazolinone.

The expression vector systems of the present invention can be used under suitable conditions to transform virtually any plant cell. Transformed cells can be regenerated into whole plants so that when a gene is expressed in intact plants, it imparts herbicide resistance to the transgenic plant.

The DNA sequence encoding the AHAS small subunit may be used in vectors to transform plants so the plants created have enhanced resistant to herbicides, particularly imidazolinones. The DNA sequence encoding the AHAS small subunit protein may be used in vectors alone or in combination with a DNA sequence encoding the large subunit of the AHAS enzyme in conferring herbicide resistance in plants.

The invention also relates to a plant expression vector comprising a eukaryotic promoter and a DNA sequence encoding a eukaryotic AHAS small subunit protein. The eukaryotic promoter for use in the expression vector should be a high level expression plant promoter, such as the *Arabidopsis* AHAS small subunit promoter. The AHAS small subunit gene sequences preferably used in the expression vector is a DNA sequence which encodes the *Arabidopsis* small subunit protein.

In another embodiment, the plant expression vector comprises a promoter for the large subunit of eukaryotic AHAS protein; a DNA sequence encoding the large subunit of a eukaryotic AHAS protein; a promoter for the small subunit of the AHAS protein; and a DNA sequence encoding for a small subunit of a eukaryotic AHAS protein.

In yet another embodiment, the plant expression vector for expressing a heterologous AHAS gene in a plant, comprises a plant promoter and a DNA sequence encoding a fusion protein comprising a large subunit and a small subunit of a eukaryotic AHAS protein.

In one embodiment, the plant expression vector comprises the *Arabidopsis* AHAS small subunit promoter and a DNA sequence encoding an *Arabidopsis* small subunit AHAS protein.

In another embodiment, the plant expression vector comprises in series a promoter expressible in a plant cell; a DNA sequence encoding a transit AHAS large subunit polypeptide; a DNA sequence encoding a wild type, mature AHAS large subunit protein or variant; a DNA sequence encoding a linker polypeptide transcript; a DNA sequence encoding a mature eukaryotic AHAS small subunit protein; and a plant terminator sequence. In this embodiment, the promoter, the DNA sequence encoding the transit AHAS large subunit protein and the DNA sequence encoding the mature AHAS large subunit protein which are preferably derived from a dicotyledoneous plant, particularly from *Arabidopsis*. Alternatively, the plant expression vector may comprise a promoter, a DNA sequence encoding the transit AHAS large subunit protein and a DNA sequence encoding the mature AHAS large subunit protein are derived from a monocotyledonous plant such as maize.

In another embodiment, the plant expression vector comprises a promoter suitable for expression in plants, a DNA sequence encoding a fusion protein comprising a large subunit and a small subunit of a eukaryotic AHAS protein.

In another embodiment, the plant expression vector comprises DNA sequences for enhancing gene expression, such as introns and leader sequences. In this aspect of the invention, the plant expression vector comprises a DNA sequence for regulating AHAS gene expression. The intron sequences may also be a heterologous intron sequence from an intron such as the maize Adh1 intron and the first intron from the shrunken-1 locus. In addition, the DNA sequences for enhancing gene expression may be a leader sequence such as the W-sequence from the Tobacco Mosaic virus.

The invention also relates to an isolated eukaryotic ALAS small subunit protein. The AHAS small subunit protein has the amino acid sequence corresponding to SEQ ID NO: 2 in the Sequence Listing. This protein can be purified from, for example, *Arabidopsis* and may be used in compositions.

Also, the gene can be used to express the *Arabidopsis* small subunit protein in a microbe such as *E. coli* and purified from extracts of *E. coli*.

The invention also relates to a method for creating a transgenic plant which is resistant to herbicides, comprising transforming a plant with a plant expression vector comprising a DNA sequence encoding a eukaryotic AHAS small subunit protein.

The invention also relates to a method for imparting herbicide resistance to a plant cell, comprising co-transforming the plant cell with a first plant expression vector comprising a first plant expressible promoter, and a DNA sequence encoding the large subunit of the AHAS protein and a second plant expression vector comprising a second plant expressible promoter and a DNA sequence encoding the small subunit of an eukaryotic AHAS protein.

The invention further relates to a method for enhancing the herbicide resistance of a transgenic plant which expresses a gene encoding an AHAS large subunit protein or a mutant or variant thereof, comprising transforming the transgenic plant with a DNA sequence encoding a eukaryotic small subunit AHAS protein or a mutant or variant thereof.

The invention also relates to a method for enhancing the herbicide resistance in the progeny plants of a plant, which comprises somatically or sexually crossing the plant with a transgenic plant whose genetic complement comprises a sequence encoding a herbicide-resistant mutant of the large subunit of a eukaryotic AHAS protein, and a DNA sequence encoding the small subunit of an eukaryotic AHAS protein; and selecting for those progeny plants which exhibit herbicide resistance.

The invention also relates to the transgenic plants and progeny produced by the methods of the invention, which plants exhibit elevated resistance to imidazolinone and other herbicides.

The invention also relates to a transgenic plant whose genetic complement comprises a plant expressible gene comprising a promoter for expression in plants, a DNA sequence encoding a fusion protein comprising a large subunit and a small subunit of a eukaryotic AHAS protein and a terminator sequence which functions in plant cells.

The invention also relates to a method for identifying mutations in the plant AHAS genes which confer resistance to herbicides, comprising exposing an organism to a herbicide compound, which organism possesses a heterologous vector comprising an AHAS small subunit protein gene. In another aspect of this embodiment, the heterologous vector may comprise the AHAS large and the small subunit genes. This method is also useful as a screening system for testing the effects of herbicides on mutant forms of the AHAS enzyme.

The invention also relates to a method for identifying mutations in the plant AHAS gene(s) which alters the allosteric feedback inhibition characteristics of the enzyme. Mutations that alter the feedback characteristics of the enzyme, in either the AHAS large or small subunit genes are used to alter amino acid levels in plants, particularly of the branched chain amino acids. The method comprises: transforming a microbial strain which is deficient in AHAS enzyme activity with a plasmid expression vector comprising a mutant plant AHAS small subunit gene. A suitable microbial strain which lacks AHAS activity is *E. coli* MI262. The mutant AHAS large and small subunit genes can be generated randomly or rationally designed from protein structural models using methods previously described (Ott et al. *J. Mol. Biol.* 263: 359-368, 1996). Once the microbial strain is transformed, they are screened in minimal medium in the presence of one or two, but not three branched chain amino acids, and then the microbial strains which grow in the minimal medium are identified.

The vectors containing the AHAS small subunit gene can be incorporated into plant or bacterial cells using conventional recombinant DNA technology. Plants are grown from trans-formed plant cells and second generation plants can be obtained from the seeds of the transgenic plants. Alternatively, the vectors for transforming plants can be recombinant plant viral vectors containing an expressible AHAS small subunit protein gene. In this embodiment, the viral vectors are capable of systemically infecting the target crop plants and capable of expressing the AHAS small subunit protein in the host plant without disrupting the genome of the host.

The invention also relates to the AHAS small subunit gene promoter DNA sequences. In this aspect of the invention, AHAS small subunit promoter sequences can be used to express heterologous polypeptides. Alternatively, the AHAS small and large subunit promoters can also be used as a coordinately regulated gene system to express heterologous multi-subunit proteins or to overexpress a single gene.

Identification, Cloning and Sequencing of the AHAS Small Subunit Protein Gene

The EST sequence of the putative *Arabidopsis thaliana* small subunit protein, designated P_12197 in the GenBank, was used to clone the complete AHAS small subunit gene. Synthetic polymerase chain reaction (PCR) primers were specifically designed to correspond to the putative AHAS small subunit DNA sequences of *Arabidopsis* corresponding to the AHAS small subunit EST sequences in deposit in the GenBank. The primers were synthesized using standard techniques (U.S. Pat. No. 4,683,202; Sambrook et al. Molecular Cloning $2^{nd}$ Ed., Cold Spring Harbor).

Reverse Transcriptase (RT)-PCR was performed on total RNA isolated from *Arabidopsis*. Primers designed from the EST sequence were able to amplify an *Arabidopsis* cDNA fragment. This fragment was cloned into an Invitrogen TA vector (Invitrogen Cat. No. K2000-01) using standard techniques. This clone was named pDGR102 and corresponded to a 450 base-pair fragment containing a portion of the EST sequence.

The same PCR primers were also used to amplify a fragment from an *Arabidopsis* λ:yes cDNA library. This confirmed that an AHAS small subunit gene was present in the library. Using a sense strand primer specific within pDGR102, and a reverse primer that hybridized to the λ:yes phagemid vector, a fragment that represented the 3' half of the small subunit gene was amplified by PCR utilizing the *Arabidopsis* total cDNA library as a template source. This product of approximately 800 bases was cloned into the Invitrogen TA vector (Invitrogen, Cat. No. K2000-01) and named clone pDGR106. Clone pDGR106 was also sequenced, and its translated amino acid sequence confirmed that the fragment represented the 3' half of the small subunit gene by homology to known prokaryotic small subunit gene sequences. This fragment contained the stop codon and 3' flanking poly A tail.

The PCR fragment contained in pDGR102 and pDGR106 were found to represent a 5' region and the 3' half, respectively, of the small subunit gene, and their DNA sequences overlapped by approximately 188 bp. A unique Ssp I restriction enzyme site located in the overlap region was used to cleave and ligate the fragment together to reconstruct a nearly full-length AHAS small subunit gene (a portion of the N-terminal gene was still missing). The resulting clone was labeled pDGR115.

5' Rapid Amplification of cDNA Ends (5' RACE, GIBCO/BRL Cat. No. 18374-058) was used to complete sequencing of the 5' end of the *Arabidopsis* AHAS small subunit gene. Primers designed from the pDGR115 sequence were used to clone and extend the sequence to the 5' end of the small subunit gene. Total RNA extracted from *Arabidopsis* seedling were used as template. The sequence was extended 650 base pairs and a putative start codon for the N-terminal methionine residue was identified. The established full length sequence was used to generate a full length cDNA clone.

A genomic clone to the *Arabidopsis* small subunit gene was obtained by screening a Clonetech *Arabidopsis* genomic lambda library. To screen the library, a 380 bp probe was generated by PCR amplification of a 5' region of the small subunit cDNA gene sequences. The PCR product was obtained by using the primers; 5'-CAGAGATCATGTG-GCTAGTTGA-3' (SEQ ID NO: 4 in the Sequence Listing) and 5'-GAGCGTCGAGAATACGATGTAC-3' (SEQ ID NO: 5 in the Sequence Listing). The 380 base pair PCR product was cloned into the Invitrogen TA cloning vector. To label the probe the PCR insert was cut out by Eco RI and labeled with $\alpha$-$^{32}$P dCTP by random priming. Screening of the library was performed on nylon membranes by conventional methods. A lambda phage hybridizing to the probe was identified and isolated. The lambda phage DNA was extracted and digested with Sal I and the fragments were cloned into pUC19. A primer specific to the small subunit cDNA sequence was used in sequencing reactions with the various cloned Sal I genomic fragment in order to identify the clone containing the small subunit gene. A clone containing AHAS small subunit sequence within a 5.6 kb Sal I fragment was identified and it is illustrated within the pMSg6 plasmid in FIG. 1. The promoter region, the transit sequence, the mature coding sequence of the small subunit gene, the introns, and the translational terminator were identified by sequencing 4.9 kb of the genomic fragment.

Through comparison of the genomic and cDNA sequences the start codon for the N-terminal methionine was identified. The cDNA for the small subunit gene codes for a polypeptide of 491 amino acids.

Figure 2:
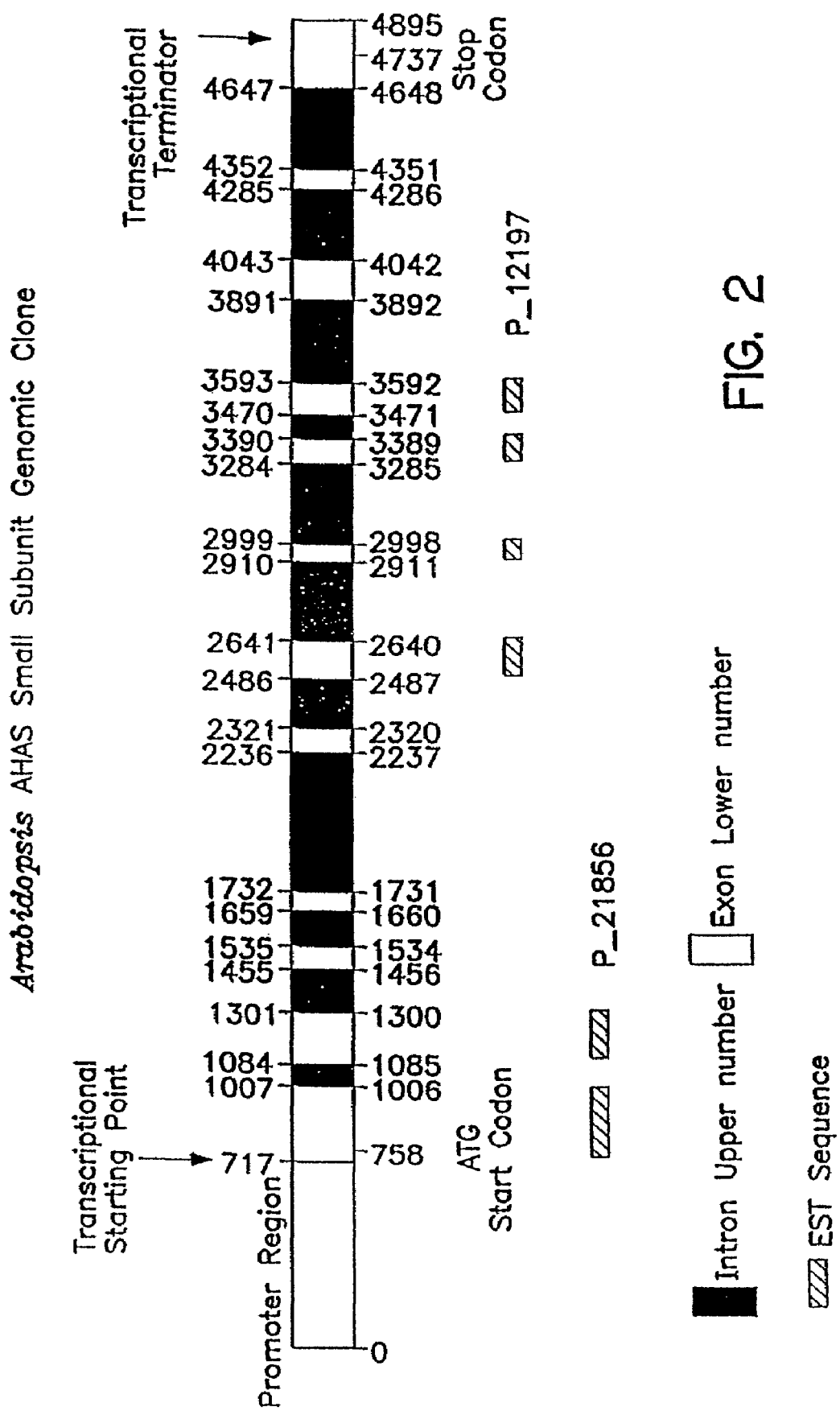
FIG. 2 depicts an *Arabidopsis* AHAS small subunit gene map.

FIG. 2 is a map of the genomic DNA sequences of the *Arabidopsis* AHAS small subunit gene. As shown in FIG. 2, and referring to SEQ ID NO: 3 in the Sequence Listing, this gene contains a promoter which extends from nucleotide number 1 to nucleotide 757. The start codon for the gene corresponds to nucleotides 758-760. The gene contains 11 introns and 12 exons. Exon 1 extends from nucleotide 758 to nucleotide 1006. Intron 1 extends from nucleotide 1007 to nucleotide 1084. Exon 2 extends from nucleotide 1085 to nucleotide 1300. Intron 2 extends from nucleotide 1301 to nucleotide 1455. Exon 3 extends from nucleotide 1456 to nucleotide 1534. Intron 3 extends from nucleotide 1535 to nucleotide 1659. Exon 4 extends from nucleotide 1660 to nucleotide 1731. Intron 4 extends from nucleotide 1732 to nucleotide 2236. Exon 5 extends from nucleotide 2237 to nucleotide 2320. Intron 5 extends from nucleotide 2321 to nucleotide 2486. Exon 6 extends from nucleotide 2487 to nucleotide 2640. Intron 6 extends from nucleotide 2641 to nucleotide 2910. Exon 7 extends from nucleotide 2911 to nucleotide 2998. Intron 7 extends from nucleotide 2999 to nucleotide 3284. Exon 8 extends from nucleotide 3285 to nucleotide 3389. Intron 8 extends from nucleotide 3390 to nucleotide 3470. Exon 9 extends from nucleotide 3471 to nucleotide 3592. Intron 9 extends from nucleotide 3593 to nucleotide 3891. Exon 10 extends from nucleotide 3892 to nucleotide 4042. Intron 10 extends from nucleotide 4043 to nucleotide 4285. Exon 11 extends from nucleotide 4286 to nucleotide 4351. Intron 11 extends from nucleotide 4352 to nucleotide 4647. Exon 12 extends from nucleotide 4648 to the stop codon at nucleotide 4737. The transcriptional terminator is located in the DNA segment between the stop codon at nucleotide 4737 and nucleotide 4895.

The amino acid sequence of the *Arabidopsis* AHAS small subunit protein encoded by the DNA sequence as described above, has high homology to amino acid sequences of AHAS small subunit proteins from prokaryotic organisms. Homology is particularly high in conserved regions of AHAS small subunit sequences in prokaryotes. As an example, the *Arabidopsis* AHAS small subunit gene sequence of the present invention had 42.5% sequence identity to that of the *Bacillus subtilis* small subunit gene. This indicated that the genomic clone DNA sequences was that of the *Arabidopsis* AHAS small subunit.

FIG. 2 also shows the location of two Genbank EST sequences with accession numbers P_12197 and P_21856. Both EST sequences had previously been identified to have homology to microbial AHAS small subunit genes, suggesting there were two isozymes in *Arabidopsis*. The EST sequence from P_12197 was used to clone the AHAS small subunit cDNA and genomic clones of the invention. Analysis of the completed AHAS sequences indicated the gene codes for two repetitive amino acid sequences with homology to known AHAS small subunits. The AHAS gene sequences are ordered in tandem within the single polypeptide. After comparing the AHAS small subunit gene sequences with the original two ESTs, it was determined that the two ESTs are part of the same gene, each corresponding to similar regions within each repeated sequence.

Some specific Materials and Methods used for cloning the genomic small subunit gene. *Arabidopsis* genomic library— *Arabidopsis* genomic library was bought from Clontech.

Construction of Plasmids Containing the AHAS Small Subunit Gene

DNA molecules containing the AHAS small subunit gene comprising the nucleotide sequence in SEQ ID NO:1 or SEQ ID NO:3 in the Sequence Listing, or a functional variant thereof, can be inserted into a suitable heterologous expression vector system in proper orientation and correct reading frame. Numerous vector systems, such as plasmids, bacteriophage viruses and other modified viruses, can be used in practicing the invention. Suitable plasmid vectors include, but are not limited to, pBR322, pUC8, pUC9, pUC18, pUC19, pBI122, pKC37, pKC101 and TA cloning vectors. Viral vectors such as λgt10, λgt11 and Charon 4 can also be used.

Construction of F1, F2, F3, pHUWE82, and pHUWE83 Plasmid Expression Vectors

Figure 3:
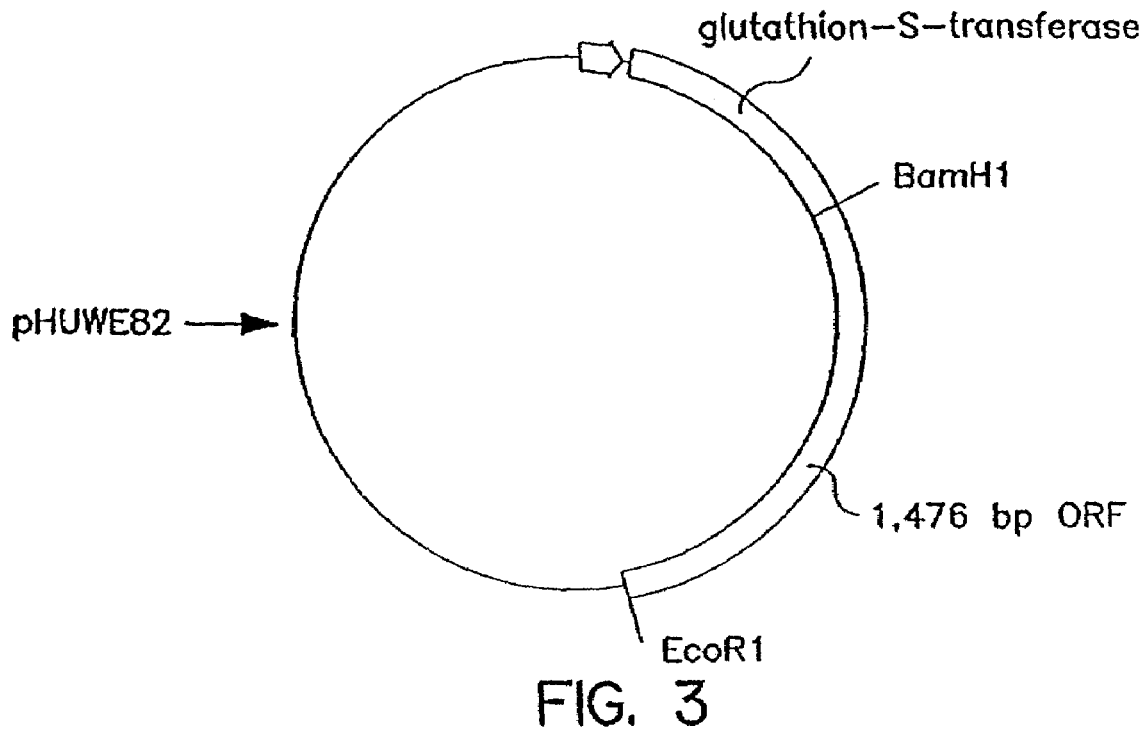
FIG. 3 depicts a plasmid expression vector, pHUWE82 of the invention, which contains the *Arabidopsis* AHAS small subunit gene without the first three codons.
Figure 4:
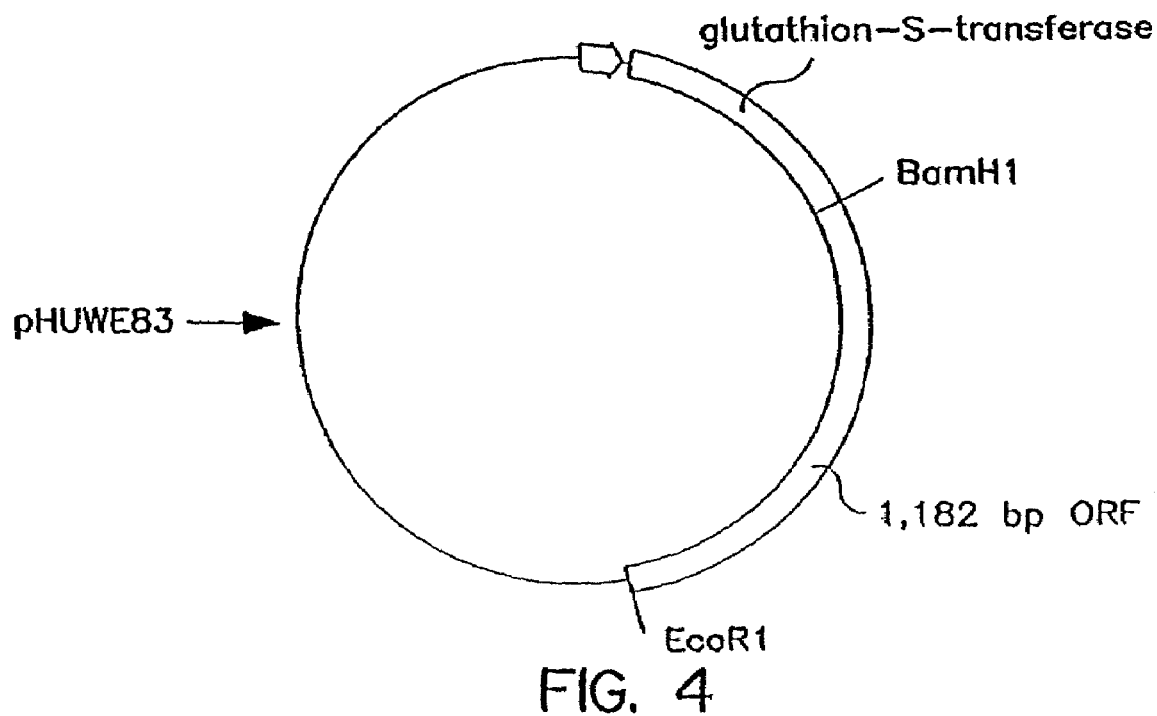
FIG. 4 depicts a plasmid expression vector, pHUWE83 of the invention, which contains the *Arabidopsis* AHAS small subunit gene minus the nucleotide sequence coding for the first 98 amino acids.

In the present invention, AHAS small subunit cDNA sequences were inserted into a pGEX-2T or pGEX4T-2 *E. coli* expression vector obtained from Pharmacia. Five different DNA fragments containing the AHAS small subunit gene sequences were cloned into the pGEX-2T or pGEX-4T-2 expression vectors. These clones were designated F1, F2, F3, pHUWE82, and pHUWE83 all differing in the amount of coding sequence contained within the expression vector. Plasmids F1, F2 and F3 contain the AHAS small subunit cDNA in pGEX-4T-2 *E. coli* expression vector and are described in more detail in Example 2 below. The AHAS small subunit cDNA in plasmids pHUWE82 and pHUWE83 was cloned in pGEX-2T *E. coli* expression vectors. The pHUWE82 vector contained a near full length *Arabidopsis* AHAS small subunit gene (without the first 3 amino acids). pHUWE83 was engineered to express the small subunit gene without the putative transit sequence (without the first 98 amino acids). A map of the plasmids pHUWE82 and pHUWE83 are shown in FIGS. 3 and 4, respectively. The versions of the small subunit gene are expressed in *E. coli* as a glutathione transferase/AHAS small subunit fusion protein. After affinity purification of the fusion protein the respective proteins are cleaved by thrombin. Due to the incorporation of the five amino acid thrombin cleavage site, i.e., Leu-Val-Pro-Arg-Gly-Ser- (SEQ ID NO:6 in the Sequence Listing), and the location of protease cleavage, an additional glycine and serine residue is maintained on the N-terminal of the small subunit protein. The resulting AHAS small subunit protein from pHUWE82 has the N-terminal sequence Gly-Ser-Ile-Ser-Val-Ser (SEQ ID NO:7 in the Sequence Listing; the first 3 amino acids Met-Ala-Ala were not incorporated into the vector), and the protein from pHUWE83 has the N-terminal sequence Gly-Ser-Met-Ile-Asn-Arg (SEQ ID NO:8 in the Sequence Listing; the first 98 amino acids were not incorporated into the vector). In both pHUWE82 and pHUWE83 the N-terminal sequence amino acids Gly-Ser- are remnants of the thrombin cleavage site.

Construction of Plant Transformation/Expression Vectors

Numerous plant transformation vectors and methods for transforming plants are available (An, G. et al. *Plant Physiol.*, 81:301-305, 1986; Fry, J., et al. *Plant Cell Rep.* 6:321-325, 1987; Block, M. *Theor. Appl. Genet.* 76:767-774, 1988; Hinchee, et al. *Stadler. Genet. Symp.* 203212.203-212, 1990; Cousins, et al. *Aust. J. Plant Physiol.* 18:481-494, 1991; Chee, P. P. and Slightom, J. L. *Gene.* 118:255-260, 1992; Christou, et al. *Trends. Biotechnol.* 10:239-246, 1992; D'Halluin, et al., *Bio/Technol.* 10:309-314. 1992; Dhir, et al. *Plant Physiol* 99:81-88, 1992; Casas et al. *Proc. Nat. Acad. Sci. USA* 90:11212-11216, 1993; Christou, P. *In Vitro Cell. Dev. Biol.—Plant;* 29P: 119-124, 1993; Davies, et al. *Plant Cell Rep.* 12:180-183, 1993; Dong, J. Z. and Mchughen, A. *Plant Sci.* 91:139-148, 1993; Franklin, C. I. and Trieu, T. N. *Plant. Physiol.* 102:167, 1993; Golovkin, et al. *Plant Sci.* 90:41-52, 1993; Guo Chin Sci. *Bull.* 38:2072-2078. 1993; Asano, et al. *Plant Cell Rep.* 13, 1994; Ayeres N. M. and Park, W. D. *Crit. Rev. Plant. Sci.* 13:219-239, 1994; Barcelo, et al. *Plant. J.* 5:583-592, 1994; Becker, et al. *Plant. J.* 5:299-307, 1994; Borkowska et al. *Acta. Physiol. Plant.* 16:225-230, 1994; Christou, P. *Agro. Food. Ind Hi Tech.* 5: 17-27, 1994; Eapen et al. *Plant Cell Rep.* 13:582-586, 1994; Hartman, et al. *Bid-Technology* 12: 919923, 1994; Ritala, et al. *Plant. Mol. Biol.* 24:317-325, 1994; Wan, Y. C. and Lemaux, P. G. *Plant Physiol.* 104:3748, 1994; Weeks, et al. *J. Cell Biochem:*104, 1994). The AHAS small subunit DNA sequences are inserted into any of the vectors using standard techniques. The selection of the vector depends on the preferred transformation technique and the target plant species to be transformed. In a preferred embodiment, the AHAS small subunit gene can be cloned behind a high level expressing plant promoter, and this construct can then be introduced into a plant that is already transgenic or a plant to be transformed with an herbicide resistant mutant allele of the large subunit protein. In this manner, the effectiveness of the herbicide resistance gene may be enhanced by stabilization or activation of the large subunit protein. This method may be applied to any plant species; however, it is most beneficial when applied to important crops.

Methodologies for constructing plant expression cassettes and introducing foreign DNA into plants is generally described in the art. For example, foreign DNA can be introduced into plants, using tumor-inducing (Ti) plasmid vectors. Other methods utilized for foreign DNA delivery involve the use of PEG mediated protoplast transformation, electroporation, microinjection whiskers, and biolistics or microprojectile bombardment for direct DNA uptake. Such methods are known in the art. (U.S. Pat. No. 5,405,765 to Vasil et al.; Bilang et al. (1991) *Gene* 100: 247-250; Scheid et al., (1991) *Mol. Gen. Genet,* 228: 104-112; Guerche et al., (1987) *Plant Science* 52: 111-116; Neuhause et al., (1987) *Theor. Appl. Genet.* 75: 30-36; Klein et al., (1987) *Nature* 327: 70-73; Howell et al., (1980) *Science* 208:1265; Horsch et al., (1985) *Science* 227: 1229-1231; DeBlock et al., (1989) *Plant Physiology* 91: 694-701*; Methods for Plant Molecular Biology* (Weissbach and Weissbach, eds.) Academic Press, Inc. (1988) and *Methods in Plant Molecular Biology* (Schuler and Zielinski, eds.) Academic Press, Inc. (1989). The method of transformation depends upon the plant cell to be transformed, stability of vectors used, expression level of gene products and other parameters.

The components of the expression cassette may be modified to increase expression of the inserted gene. For example, truncated sequences, nucleotide substitutions or other modifications may be employed. DNA sequences for enhancing gene expression may also be used in the plant expression vectors. These include the introns of the maize Adh1, intron 1 gene (Callis et al. Genes and Development 1:1183-1200, 1987), and leader sequences, (W-sequence) from the Tobacco Mosaic virus (TMV), Maize Chlorotic Mottle Virus and Alfalfa Mosaic Virus (Gallie et al. *Nucleic Acid Res.* 15:8693-8711, 1987 and Skuzeski et al. *Plant Molec. Biol* 15:65-79, 1990). The first intron from the shrunkent-1 locus of maize, has been shown to increase expression of genes in chimeric gene constructs. U.S. Pat. Nos. 5,424,412 and 5,593,874 disclose the use of specific introns in gene expression constructs, and Gallie et al. (*Plant Physiol.* 106:929-939, 1994) also have shown that introns are useful for regulating gene expression on a tissue specific basis. To further enhance or to optimize AHAS small subunit gene expression, the plant expression vectors of the invention may also contain DNA sequences containing matrix attachment regions (MARs). Plant cells transformed with such modified expression systems, then, may exhibit overexpression or constitutive expression of the AHAS small subunit gene.

To obtain efficient expression of the AHAS small subunit gene and other genes of the present invention, a promoter must be present in the expression vector. Depending upon the host cell system utilized, any one of a number of suitable promoters can be used. Suitable promoters should be high level expression plant promoters which include ubiquitin, nos promoter, the small subunit ribulose bisphosphate carboxylase gene promoter, the small subunit chlorophyll A/B binding polypeptide promoter, the 35S promoter of cauliflower mosaic virus, the AHAS large and small subunit promoters, (OCS)3 MAS and promoters isolated from plants and plant viruses. See C. E. Vallejos, et al., "Localization in the Tomato Genome of DNA Restriction Fragments Containing Sequences Homologous to the $_R$RNA (45S), the major chlorophyll $_{A/B}$binding Polypeptide and the Ribulose Bisphosphate Carboxylase Genes," *Genetics* 112: 93-105 (1986). Another promoter suitable for transforming plants is the actin promoter. A preferred promoter of the invention is the AHAS small subunit promoter for use with the AHAS small subunit gene sequences. The expression vector can then be used to transform a plant cell. Other plant tissues suitable for transformation include leaf tissues, root tissues, meristems, cultured plant cells such as calluses, and protoplasts.

Use of the AHAS small subunit gene promoter: In a preferred embodiment, the promoter to be used to transcribe the AHAS small subunit gene should be a strong plant promoter. The native promoter of the AHAS small subunit gene in plants may be used for expressing the AHAS small subunit protein gene in transgenic plants. The small subunit gene promoter can also be used in vectors to express heterologous genes. The AHAS small subunit promoter can also be used in vectors in conjunction with the promoter of the AHAS large subunit gene. These promoters, which would drive the transcription of the two genes coding for two subunits of a single multimeric protein, may be utilized as coordinately regulated promoters. For example, both promoters may be upregulated simultaneously at a specific time or in a specific tissue such as meristems. The advantage of two different, but simultaneously, active promoters is that they may not be susceptible to co-suppression. Co-suppression can occur when two genes of similar sequence are present within a transformed organism. Co-suppression causes the same level of silencing of expression of the genes.

Moreover, a transformation vector containing two genes regulated with the same promoter sequence can undergo recombination between like sequences, thereby inactivating one or both genes. Use of different promoters that are co-regulated may allow for expression of two genes without problems of recombination, and facilitates the expression of multimeric proteins.

The promoter of the AHAS small subunit gene can be used for additional purposes. First, the large and the small subunit genes code for polypeptides that work in concert and in physical contact with each other, the two genes may be coordinately regulated in expression. Having both the large and small subunit promoter may enable the expression of other multimeric proteins, or overexpression of the same gene from two different promoters. This is advantageous since expressing two genes with the same promoter may cause problems due to recombination of homologous promoter sequences. If two different promoters are used, genes for multimeric proteins may not be expressed at the same time or in the same tissue. Coordinately regulated but heterologous promoters would overcome these problems.

Secondly, having both the large and small subunit promoter provides tools to understand gene regulation. These promoters can be ligated to reporter genes to test for determining the coordination of the level, tissue specificity, and coordination of subunit genes.

Thirdly, it is advantageous to express the small subunit gene on its own promoter so that it is expressed at the appropriate time and tissue to have the most effect in enhancing herbicide resistance.

Lastly, having two promoters that may be coordinately regulated provides us with a tool for analyzing, and isolating regulatory factors that may be common to each of the promoters. Such factors include transcription factors that regulate expression from both AHAS large and small subunit promoters. The promoter sequences may also have common motifs that may be involved in coordinate regulation of the two genes. Moreover, the role of introns in the small subunit genomic clone may be involved in co-regulation of the two promoters. The two promoters and the introns provide us with tools to elucidate the mechanism of coordinate regulation of promoters.

Use of Introns of AHAS Small Subunit Gene

The genomic clone has several introns which may be used to regulate gene expression. Introns have been shown to regulate gene expression. For example the maize Adh1 intron 1 significantly increases expression of reporter genes in maize (Callis et al. 1987, Genes & Development 1:1183-1200 by Cold Spring Harbor Laboratory ISSN 0890-9369/87). The first intron of the shrunkent-1 locus of maize has also been shown to increase expression in chimeric gene constructs. U.S. Pat. Nos. 5,424,412 and 5,593,874 disclose the use of specific introns for regulating gene expression.

Introns have also been shown to regulate the level of expression on a tissues specific basis. Gallie et al. (Plant Physiol. 106:929-939) showed that enhancement of gene expression by introns is dependent on cell type. Therefore, the AHAS small subunit gene introns can be used to express genes with particular emphasis in specific tissue types.

It is also advantageous to express the small subunit gene with all of its introns so that it is expressed at the appropriate time and tissue to have the most effect in enhancing herbicide resistance.

Use of the AHAS Small Subunit Gene in Expression Vectors

Tethered enzyme. In this embodiment of the invention, the AHAS small subunit is translationally coupled to the large subunit via a transcript coding for a linker polypeptide, such as polyglycine (polyGly). The length of the linker polypeptide tether is varied. The positioning of the two AHAS subunits with respect to the linker polypeptide tether is the large subunit transit sequence followed by the large subunit mature coding sequence, the linker polypeptide transcript, and the small subunit mature coding sequence. An alternative positioning involves switching the mature coding sequences of the large and small subunits about the linker polypeptide transcript with the small subunit transit sequence.

Tethered enzymes to enhance activity and herbicide resistance. It has been shown with the E. coli enzyme that the association between large and small subunits is loose. It was estimated that in E. coli at a concentration of $10^{-7}$M for each subunit, the large subunits are only half associated as the $\alpha_2\beta_2$ active holoenzyme (Sella et al. 1993, J. Bacteriology 175: 5339-5343). Greatest activity is achieved in molar excesses of the AHAS small subunit protein. Since it has been determined that the AHAS enzyme is most stable and active when both subunits are associated (Weinstock et al 1992, J. Bacteriology, 174:5560-5566, Sella et al. 1993, J. Bacteriology 175: 5339-5343) a highly active and stable enzyme may be created by fusing the two subunits into a single polypeptide. Tethered polypeptides have been shown to function properly. Gilbert et al. expressed two tethered oligosaccharide synthetic enzymes in E. coli to produce an enzyme that was functional, stable in vitro, and soluble (Gilbert et al. Nature Biotechnology 16: 769-772, 1998).

Expression of both the large and small subunits of AHAS as a single polypeptide from a single gene also has advantages for producing transgenic herbicide resistant crops. The use of a single gene to transform and breed plants into elite crop lines is easier and more advantageous than when two or more genes are used.

Fused enzyme pair. In this aspect of the invention, the AHAS small subunit is positioned in the plant vector directly downstream of the large subunit under the direction of a single promoter. Alternatively, the small and large subunit genes of AHAS can be separated and put under the direction of different promoters within a single construct.

Two genes, one construct. In another aspect of the invention, in this expression vector, both the large and the small subunit of AHAS are placed under the control of separate promoters, in a single plasmid construct. This enables the expression of both genes as separate entities; however, the tandem would behave in the plant progeny as a single locus.

Two genes, one promoter. The maize streak virus promoter is a bi-functional promoter able to express genes in two direction. Using this promoter, gene transcription can be initiated on genes coded on opposite strands in the vector and in opposite directions. Therefore, a large and a small subunit genes of AHAS can be expressed from a single promoter.

Two genes, two constructs. In another approach, two separate vector constructs are made, each containing either the large or small subunit under the direction of different promoters. This approach requires that the plant be doubly transformed.

The plant expression vector should also contain a suitable transcription terminator sequence downstream from the gene sequences. A variety of transcriptional terminators are known for use in plant expression cassettes for correct termination of gene transcription and polyadenylation of the transcript. Terminators for use in the invention include CaMV 35S terminator, the nopaline synthase terminator, the pea bcs terminator, the tml terminator, the AHAS large and small subunit terminators. These terminators can be used in vectors for use in both monocotyledon and dicotyledon transformation.

The gene products of the invention may also be targeted to the chloroplasts. This is accomplished by introducing a signal sequence which can be fused into the gene and thus into the expression vector. The signal sequence which will correspond to the amino terminal end of the gene product (see Comai et al. *J. Biol. Chem.* 263:15104-15109, 1988) is fused into the upstream 5' end of the gene. The AHAS small subunit protein of the invention has been found to possess a signal sequence, and therefore, this signal sequence can be used in the vectors of the invention. Other signal sequences for use in the invention are known, such as those from the 5' end of cDNAs from the AHAS large or small subunit, CAB protein, the EPSP synthase, the GS2 protein, and the like (Cheng & Jogendorf, *J. Biol. Chem.* 268:2363-2367, 1993).

Bacteria from the genus *Agrobacterium* can be utilized to introduce foreign DNA and transform plant cells. Suitable species of such bacterium include *Agrobacterium tumefaciens* and *Agrobacterium rhizogenes*. *Agrobacterium tumefaciens* (e.g., strains LBA4404 or EHA105) is particularly useful due to its well-known ability to transform plants.

Another approach to transforming plant cells with a heterologous gene involves propelling inert or biologically active particles at plant tissues and cells. U.S. Pat. Nos. 4,945,050; 5,036,006; and 5,100,792 all to Sanford et al. disclose this technique. In summary, this procedure involves propelling inert or biologically active particles at the cells under conditions effective to penetrate the outer surface of the cell in such manner as to incorporate the vectors into the interior of the cells. When inert particles are utilized, the vector can be introduced into the cell by coating the particles with the vector containing the desired gene. Alternatively, the target cell can be surrounded by the vector so that the vector is carried into the cell by the wake of the particle. Other biologically active particles including dried yeast cells, dried bacteria, or bacteriophages, each containing the desired DNA, can also be propelled into plant cell tissue. In addition, the vectors of the invention can be constructed so that they are suitable for use in plastid transformation methods using standard techniques.

The isolated AHAS small subunit gene of the present invention can be utilized to confer herbicide resistance to a wide variety of plant cells including monocots and dicots. Although the gene can be inserted into any plant cell falling within these broad classes, it is particularly useful in crop plant cells, such as those of rice, wheat, barley, rye, corn, carrot, sugarcane, tobacco, bean, pea, soybean, sugar beet, and canola.

The expression system of the present invention can be used to transform virtually any crop plant cell under suitable conditions. Transformed cells can be regenerated into whole plants such that the AHAS small subunit gene imparts or enhances herbicide resistance to the intact transgenic plants. As set forth above, the expression system can be modified so that the herbicide resistance gene is continuously or constitutively expressed.

Use of the AHAS small subunit gene to enhance herbicide resistance in plants: A plasmid that contains both the genes for the AHAS large and small subunit can be constructed. In this manner, the two genes would segregate as a single locus making breeding of herbicide resistant crops easier. Alternatively, the large and small subunit can be fused into a single gene expressed from a single promoter. The fusion protein would have elevated levels of activity and herbicide resistance. The large subunit of AHAS may be of a wild type sequence (if resistance is conferred in the presence of an independent or fused small subunit), or may be a mutant large subunit that in itself has some level of resistance to herbicides. The presence of the small subunit will 1) enhance the activity of the large subunit, 2) enhance the herbicide resistance of the large subunit, 3) increase the stability of the enzyme when expressed in vivo and 4) increase resistance to large subunit to degradation. The small subunit would in this manner elevate the resistance of the plant/crop to the imidazolinone or other herbicides. The elevated resistance would permit the application and/or increase the safety of weed-controlling rates of herbicide without phytotoxicity to the transformed plant/crop. Ideally, the resistance conferred would elevate resistance to imidazolinone and other classes of herbicides without increasing, or by increasing to a lesser degree, resistance to other AHAS inhibiting herbicides such as sulfonylureas, triazolopyrimidines, etc.

Additional Aspects about Enhancing Herbicide Resistance by the Addition of the Small Subunit Gene to Plants Expressing a Herbicide Resistant Form of the Large Subunit Gene.

It has been shown in many cases that mutations in proteins can cause instability, decreases in activity, and a greater propensity to degradation. Herbicide resistant AHAS genes, particularly those from plants, generally contain a mutation that confers the resistance to inhibition by the herbicide. This places a greater level of importance in stabilizing, maintaining activity, and resistance to degradation of these proteins. The accompaniment of the small subunit gene to the large subunit gene may assist in these areas of susceptibility.

Subunits of multi-subunit proteins that are present in the absence or non-stoichiometric levels of the complementary subunits can be preferentially degraded. This has been shown for the large and small subunits of ribulosebisphosphate carboxylase/oxygenase (Spreitzer et al. *Proc. Natl. Acad. Sci. USA* 82: 5460-5464). If the large subunit gene for AHAS is transformed and expressed in a crop that does not have the complementary small subunit, or is expressed at high levels beyond the expression levels of the small subunit gene, the large subunit protein could be unstable and preferentially degraded. This could result in a lower level of herbicide resistance.

The association of large and small subunits appears to be highly specific. *E. coli* has three isozymes of large subunits and three isozymes of small subunits. Each large subunit isozyme specifically associates with only one of the small subunit isozymes, even though all subunits are expressed in the same organism (Weinstock et al 1992, *J. Bacteriology*, 174:5560-5566). This specificity suggests that endogenous AHAS small subunit proteins could not stabilize or enhance the activity of an introduced AHAS large subunit if the large subunit gene is derived from a different organism or isozyme pair from that of the small subunit. This places an importance, for purposes of herbicide resistance, in introducing both the large and small subunit genes from the same organism and isozyme pair. The expression of a small subunit gene may ameliorate these problems.

The AHAS small subunit gene in combination with the AHAS large subunit gene can also be used as a marker for selecting transformant plant cells and tissues. Any gene of interest can be incorporated in vectors containing the AHAS large and small subunit genes. The vectors can be introduced into plant cells or tissues that are susceptible to AHAS-inhibiting herbicides. The transformants containing these vectors can be selected in the presence of herbicides using standard techniques.

EXAMPLE 1

DNA and Lambda DNA isolation: DNA isolation was carried out using QIAgen Spin Miniprep Kit (50) (QIAgen Cat. No. 27104) and standard procedures as provided by the manufacturer. For Lambda DNA isolation, the QIAgen Lambda Midi Kit (25) (QIAgen Cat. No. 12543) was used following the manufacture's protocol. In TA Cloning, the Invitrogen Original TA Cloning Kit (Invitrogen Cat. No. K2000-01) was used and standard protocols were followed.

Subcloning: Lambda DNA was digested with the appropriate restriction enzyme and mixed with pUC19 which was digested with the same restriction enzyme. After phenol extraction, the insert was ligated with pUC19 by adding 1 μl DNA ligase (4 units/mL) and incubate at 17° C. overnight.

5' RACE: The 5' RACE used in the experiments was 5' RACE System for Rapid Amplification of cDNA Ends and was obtained from GIBCO/BRL (Cat. No. 18374-058). The reactions were carried out following standard procedures provided by the manufacturer.

Screening library: The Clonotech *Arabidopsis* lambda genomic library was plated at a density of 30,000 plaques/150 mm plate as described in the protocol supplied by the manufacturer. Amersham Nucleic Acid Transfer Membranes Hybond™-N+ (DISC: 0.137 m DIA, Removal Rating: 0.45 um) were used. The nylon transfer membranes were carefully placed onto the plate surface, and membranes and agar were marked using a sterile needle. The first membrane was removed after 3 minutes and a duplicate membrane was placed on the plate surface and removed after 8 minutes. The membranes were placed, colony side up, on a pad of absorbent filter paper soaked in denaturing buffer (0.5N NaOH, 1.5N NaCl) for 5 minutes, then each membrane was placed, colony side up, on a pad of absorbent filter paper soaked in neutralizing solution (1M Tris-HCl, 1.5N NaCl) for 5 minutes. The membranes were washed briefly in 2×SSC, and transferred to dry filter paper. The sample was fixed to the membranes by UV crosslinking and vacuum-baked at 80° C. for 1 hour. Then the membranes were prehybridized in a buffer containing 50% formamide, 2×SSC, 5×Denhardt's solution, 1% sodium dodecyl sulfate (SDS), 0.05 mg/ml denatured salmon sperm DNA, and 0.05% NaPPi at 42° C. for 2 hour. DNA was digested with restriction enzyme and fractionated on a 1% agarose gel. The DNA fragment containing the AHAS small subunit gene was purified using QIAquick Gel Extraction Kit (50) (QIAgen Cat. No. 28704). The GIBCO/BRL Life Technologies Random Primers DNA labeling System (Cat. No. 18187-013) was used to label the DNA with the following modification. 125 ng of probe DNA was dissolved in 55 μL of distilled water in a microcentrifuge tube and denatured by heating for 5 minutes in a boiling water bath, and immediately cooled on ice. Then, dATP, dGTP, dTTP, [α-$^{32}$P]dCTP and Klenow enzyme were added to the denatured DNA, and the mixture was incubated at 25° C. for an hour. One volume of formamide was added to the mixture and the reaction was heated at 65° C. for 30 minutes. The reaction containing the labeled DNA was added to prehybridization solution and the membranes were hybridized at 42° C. for 20 hours with slow shaking. After hybridization, the membranes were washed twice with 0.4×SSC buffer containing 0.1% SDS at room temperature for 10 minutes, followed by a single wash in 0.2×SSC buffer containing 0.1% SDS at 65° C. for 30 minutes. The membranes were exposed to X-ray film overnight. Plaques containing DNA which hybridized to the DNA probe on duplicate membranes produced a positive result, and these plaques were isolated. The procedure was duplicated until single isolates could be collected.

Sequencing: The sequencing reaction was carried out using the ABI PRISM DNA sequencing Kit following the ABI protocol provided. After ethanol precipitation, the DNA was dissolved in ABI PRISM Template Suppression Reagent and denatured at 90° C. for 5 minutes. Then, the samples were loaded onto an ABI 310 sequencer.

EXAMPLE 2

Preparation of Plasmid DNA Containing AHAS Large Subunit Protein Genes

The wild type (pAC774) and Met92His mutant (pAC786) AHAS large subunit genes from *Arabidopsis* were constructed into the *E. coli* expression vector pGEX-4T-2 from Pharmacia. The genes were constructed to express a glutathione transferase/AHAS large subunit fusion protein to aid in purification, similarly as described for plasmids pHUWE82 and pHUWE83 as described above. A five amino acid protease cleavage site was encoded at the junction of the two proteins so that they could be cleaved apart after purification. Three vector constructs containing the cDNA sequences of the *Arabidopsis* AHAS small subunit gene were made using the pGEX-4T-2 expression vector. These were designated F1, F2 and F3, all three differing in the amount of peptide sequence contained within the gene. The N-terminal amino acid sequence of the peptide encoded by the AHAS cDNA of the F1 plasmid is Gly-Ser-Pro-Lys-Ile-Ala-Leu-Arg- (SEQ ID NO: 9 in the Sequence Listing). The N-terminal amino acid sequence of the peptide encoded by the AHAS cDNA of plasmid F2 is Gly-Ser-Leu-Asp-Ala-His-Trp- (SEQ ID NO: 10 in the Sequence Listing). The N-terminal amino acid sequence of the peptide encoded by the AHAS cDNA of the F3 plasmid is Gly-Ser-Val-Glu-Pro-Phe-Phe- (SEQ ID NO: 11 in the Sequence Listing). The N-terminal Gly-Ser- for all three peptides are remnants of the thrombin cleavage.

Expression of the *Arabidopsis* Large and Small Subunits Proteins of AHAS

DH5α-competent cells (Gibco BRL) were transformed with large subunit plasmids pAC774 and pAC786, as well as small subunit plasmids F1, F2, and F3. Cells were thawed on ice. 1 μl of a 1:5 dilution of the plasmid DNA was added to 75 μl of cells, which then sat on ice for 30 minutes. Cells were heat shocked in a 42° C. water bath for 90 seconds and then put on ice for two minutes. 800 μl of Luria-Bertani medium (LB) was added to each tube containing transformed cells which were then grown for 1 hour in a 37° C. shaker. Cells were centrifuged for 2 minutes and excess medium was aspirated. The cell pellet was resuspended in 100 μl of LB and plated on LB containing 100 μg of carbenicillin overnight at 37° C. Single colonies were inoculated into 50 ml of LB medium containing 375 μg/ml carbenicillin and grown overnight in a 37° C. shaker. 700 μl aliquots were taken and added to 300 μl of 50% glycerol, and were then frozen in liquid nitrogen and kept at −80° C. for cell stocks.

Purification of the Large Subunit AHAS Gene

An overnight 50 ml culture of transformed *E. coli* harboring the large subunit gene in the pGEX-2T expression vector was inoculated into 1 liter of 2×YT with 2% glucose, 375 μg/ml Carbenicillin. Cells were grown for 5 hours in a 37° C. shaker/incubator and then induced with 0.1 mM IPTG and then placed in a 30° C. shaker for another 2.5 hours. Cells were harvested by centrifugation in a JA10 rotor at 8000 rpm at 4° C. for 10 minutes. Cells were stored as a pellet at −20° C. until purification.

The cell pellet from 1 liter of cell culture was resuspended in 10 ml of MTPBS (150 mM NaCl, 16 mM $Na_2HPO_4$, 4 mM $NaH_2PO_4$), pH 7.3 (Smith and Johnson *Gene* 67: 31-40, 1998) and 100 μg/ml of lysozyme was added. The suspension was adjusted to 5 mM dithiothreitol. Triton X-100 was added to a final concentration of 1% by addition of a 20% Triton X-100 in MTPBS solution. The cells were shaken gently at 30° C. for 15 minutes and were then cooled to 4° C. on ice and sonicated for 8-10 seconds using a microtip probe, duty cycle 70%, output control at maximum for the microtip pulser. The sonicate was centrifuged two times in a J20 rotor, 17,000 rpm, 4° C., 10 minutes, to remove insoluble material. Lysate was added to 150 mg (dry weight) of glutathione agarose (equilibrated and hydrated in MTPBS) and inverted for 30 minutes at 4° C. Agarose was settled by centrifugation at 500 rpm for 5 minutes and was washed with ice cold MTPBS by repeated centrifugation cycles until the $A_{280}$ of the wash matched that of MTPBS. Agarose was transferred to an appropriate column for elution. Fusion proteins were eluted with 50 mM Tris-HCl, 5 mM reduced glutathione into 1 ml fractions. The $A_{280}$ of each fraction was checked for protein content and appropriate fractions ($A_{280}>0.100$) were pooled. To the pooled sample were added 5 units of bovine thrombin per ml of protein solution. The sample was dialyzed against MTPBS, 3 mM dithiothreitol for 15 hours at room temperature to allow proteolytic cleavage of the fusion protein and removal of Tris-HCl and reduced glutathione. Dialyzed sample was passed twice more through equilibrated glutathione agarose to remove the cleaved GST protein and to remove uncut fusion protein. Purified samples were stored at 4° C. with or without 0.02% sodium azide.

Purification of Small Subunit Protein of AHAS

Transformed DH5 cells were cultured and harvested in a manner similar to that used for collecting cells expressing the large subunit of AHAS. The cell pellet from 1 liter of culture was resuspended in 10 ml of STE (150 mM NaCl, 10 mM Tris-HCl pH 8.0, 1 mM EDTA), and then 100 μg/ml of lysozyme was added. This was put on ice for 15 minutes. Dithiothreitol was added to 5 mM and N-lauroylsarcosine was added to a final concentration of 1.5% from a 10% stock in STE. The cells were vortexed for 10 seconds. The lysate was sonicated on ice for 8-10 seconds using a microtip probe, duty cycle 70%, output control at maximum for the microtip pulser. The sonicate was centrifuged two times in a JA20 rotor at 4° C. at 17,000 rpm for 10 minutes, to remove insoluble material. The supernatant was added to 200 mg (dry weight) of glutathione agarose (equilibrated and hydrated in MTPBS) and inverted for 20 minutes at 4° C. The agarose was settled by centrifugation at 500 rpm for 5 minutes, and the supernatant was aspirated. The agarose was washed with ice cold MTPBS by repeated centrifugation cycles until the $A_{280}$ of the wash was equal to that of MTPBS. The agarose was transferred to an appropriate column for elution. Fusion proteins were eluted with 50 mM Tris-HCL pH 8.0, 10 mM reduced glutathione, 5 mM dithiothreitol, and 2% N-octylglucoside, and 1 ml fractions were collected. The absorbance at 280 nm of each fraction was checked, and appropriate fractions ($A_{280}>0.100$) were pooled. The sample was dialyzed for 15 hours against MTPBS, 3 mM dithiothreitol, at 4° C. to remove reduced glutathione, Tris-HCl, and N-octylglucoside. SDS was added to 0.005% from a 1% stock solution in $H_2O$. Five units of bovine thrombin were added per ml of protein solution, and the sample was shaken gently at room temperature for 30-45 minutes to allow proteolytic cleavage of the fusion protein. The sample was then immediately passed through an EtractiGel-D detergent affinity column (Pierce) to remove SDS. The cut sample was stored at 4° C. or passed twice through re-equilibrated glutathione agarose to remove GST and uncut fusion protein. The purified sample was stored at 4° C.

Determination of Protein Concentration

An aliquot of protein solution was adjusted to 5% trichloroacetic acid and put on ice for 20 minutes to allow precipitation of protein. The aliquot was then centrifuged for 10 minutes at high speed and 4° C. to pellet the precipitate. The pellet was resuspended in an equivalent volume of 3% (w/v) sodium carbonate, 0.1N NaOH. A Pierce BCA protein assay was used to determine the concentration of the protein solution. Bovine serum albumin standards were prepared in 3% sodium carbonate, 0.1N NaOH.

AHAS assays. AHAS assays were performed with slight modification as described by Singh et al. {Singh et al., 1988}. AHAS activity was assayed in 1×AHAS assay buffer (50 mM HEPES pH 7.0, 100 mM pyruvate, 10 mM $MgCl_2$, 1 mM TPP, and 50 μM FAD). A final concentration of 1× assay buffer was obtained either by dilution of enzyme extracted in 2× assay buffer or addition of enzyme to make a final concentration 1×AHAS assay buffer. All assays containing imazethapyr and associated controls contained a final concentration of 5% DMSO due to addition of imazethapyr to assay mixtures as a 50% DMSO solution. Assays were performed in a final volume of 250 μL at 37° C. in microtiter plates.

EXAMPLE 3

Figure 5:
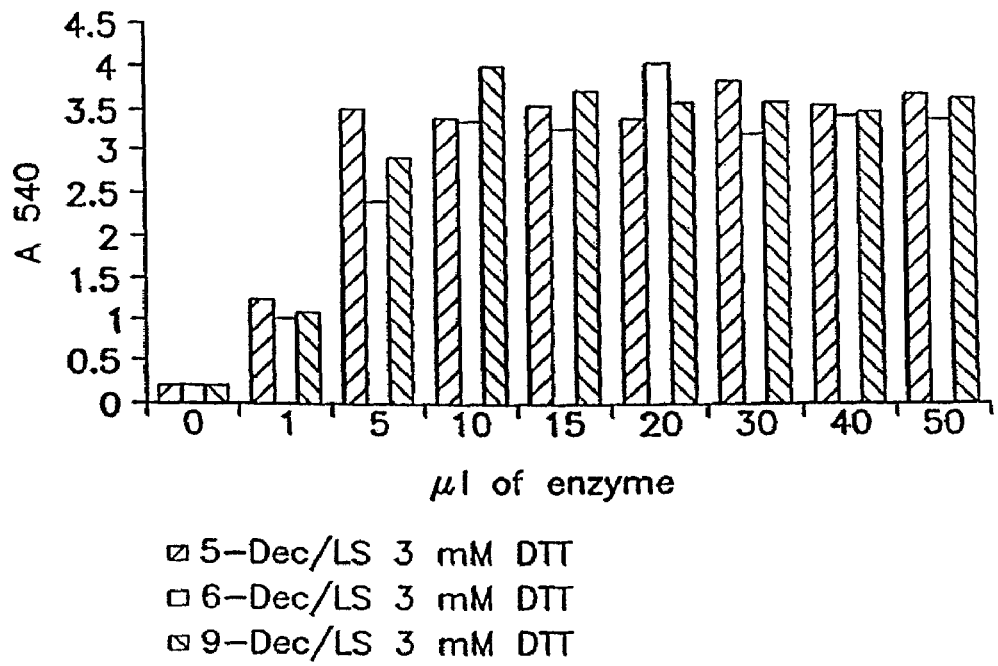
FIG. 5 is a bar graph showing the in vitro activity and stability of the large AHAS subunit protein of the *Arabidopsis* AHAS enzyme in the presence of Phosphate Buffered Saline (MTPBS) and dithiothreitol (DTT).
Figure 6:
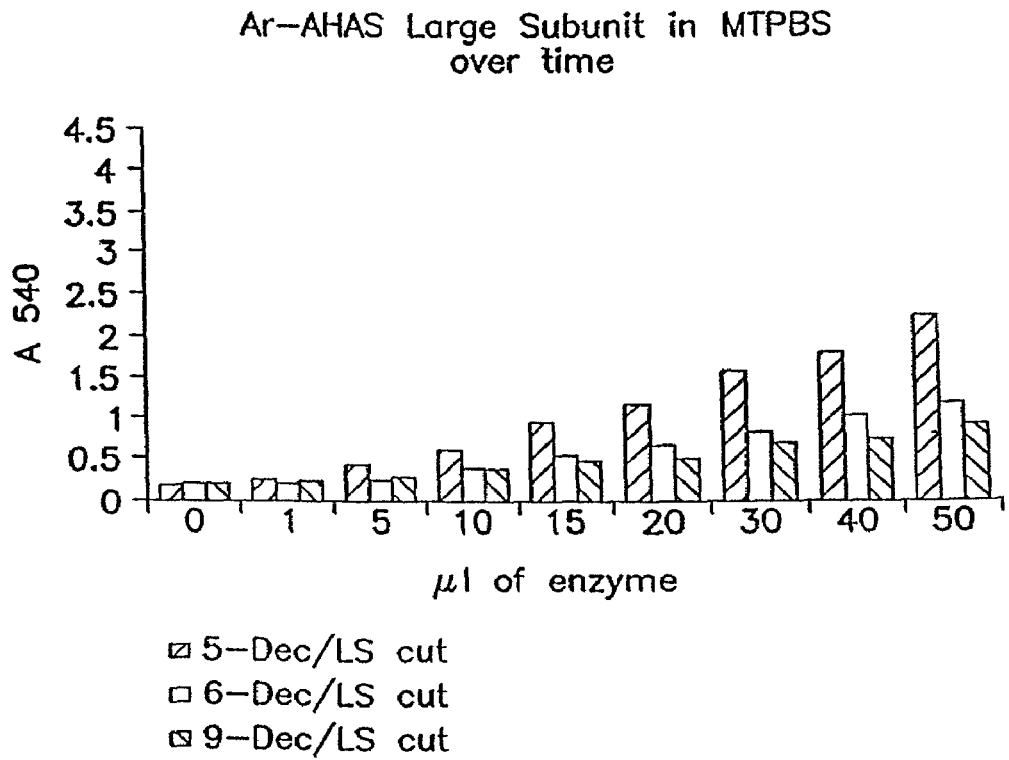
FIG. 6 is a bar graph showing the in vitro activity of the large subunit protein of the *Arabidopsis* AHAS enzyme in the presence of Phosphate Buffered Saline (MTPBS).

Effects of Dithiothreitol. The effect of dithiothreitol (DTT) in Phosphate Buffered Saline (MTPBS) on AHAS large subunit enzyme activity was measured. Experiments were carried out with or without 3 mM DTT in the purified protein solution of large subunit. The assays were conducted as above. The results are presented in FIGS. 5 and 6. As can be seen in FIG. 5 when compared to FIG. 6, the catalytic activity of the AHAS large subunit is enhanced dramatically by DTT. Moreover, in the absence of DTT, large subunit activity degraded over the 4 day period (FIG. 6). The *Arabidopsis* large subunit was found to be very stable in the presence of 3 mM DTT over a period of 1 month when stored at 4° C.

Other sulfhydryl reductants were tested, but DTT appeared to both stabilize and activate the enzyme better than reduced glutathione and β-mercaptoethanol. Due to the activation of the enzyme by DTT all experiments addressing activation of the AHAS large subunit enzyme by the small subunit enzyme were performed either in the absence of DTT or other sulfhydryl reducing agents or at a constant concentration of 3 mM DTT.

Figure 7:
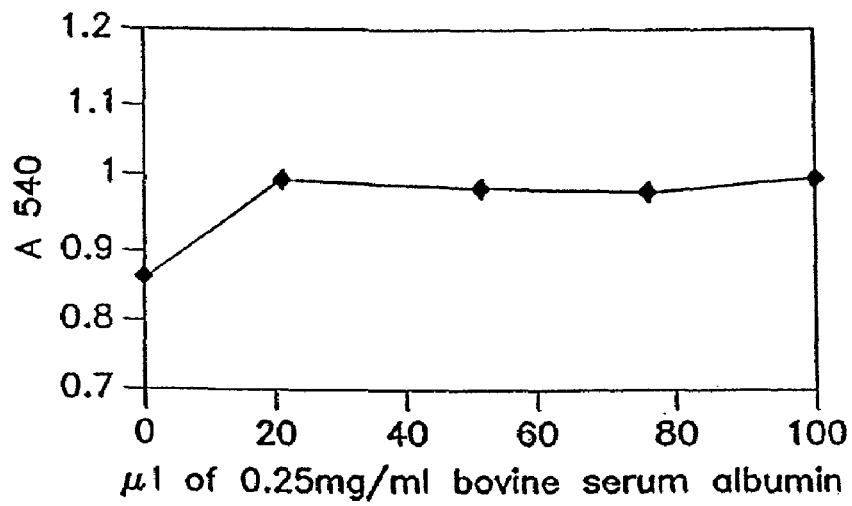
FIG. 7 is a graph showing the in vitro activity of the large subunit protein of the *Arabidopsis* AHAS enzyme in the presence of increasing amounts of bovine serum albumin (BSA).

Effects of Bovine Serum Albumin. To determine whether the enhancement of the large subunit was specific to the small subunit, another nonspecific control which tested the effects of bovine serum albumin was run. To a fixed amount of large subunit an increasing amount of a 0.25 mg/mil BSA solution was added. The results are shown in FIG. 7. As seen in FIG. 7, the addition of BSA to the test sample caused a slight, but not significant, and a plateaued increase in the catalytic activity of the large subunit protein of AHAS.

EXAMPLE 4

The following experiments used the small subunit and large subunit proteins purified as described in Example 2 above. The plasmid F1 containing the AHAS small subunit gene from *Arabidopsis* was expressed in *E. coli* and partially purified. The protein concentration of the sample was determined and aliquots of increasing concentration were added to a constant amount of purified *Arabidopsis* large subunit.

Figure 8:
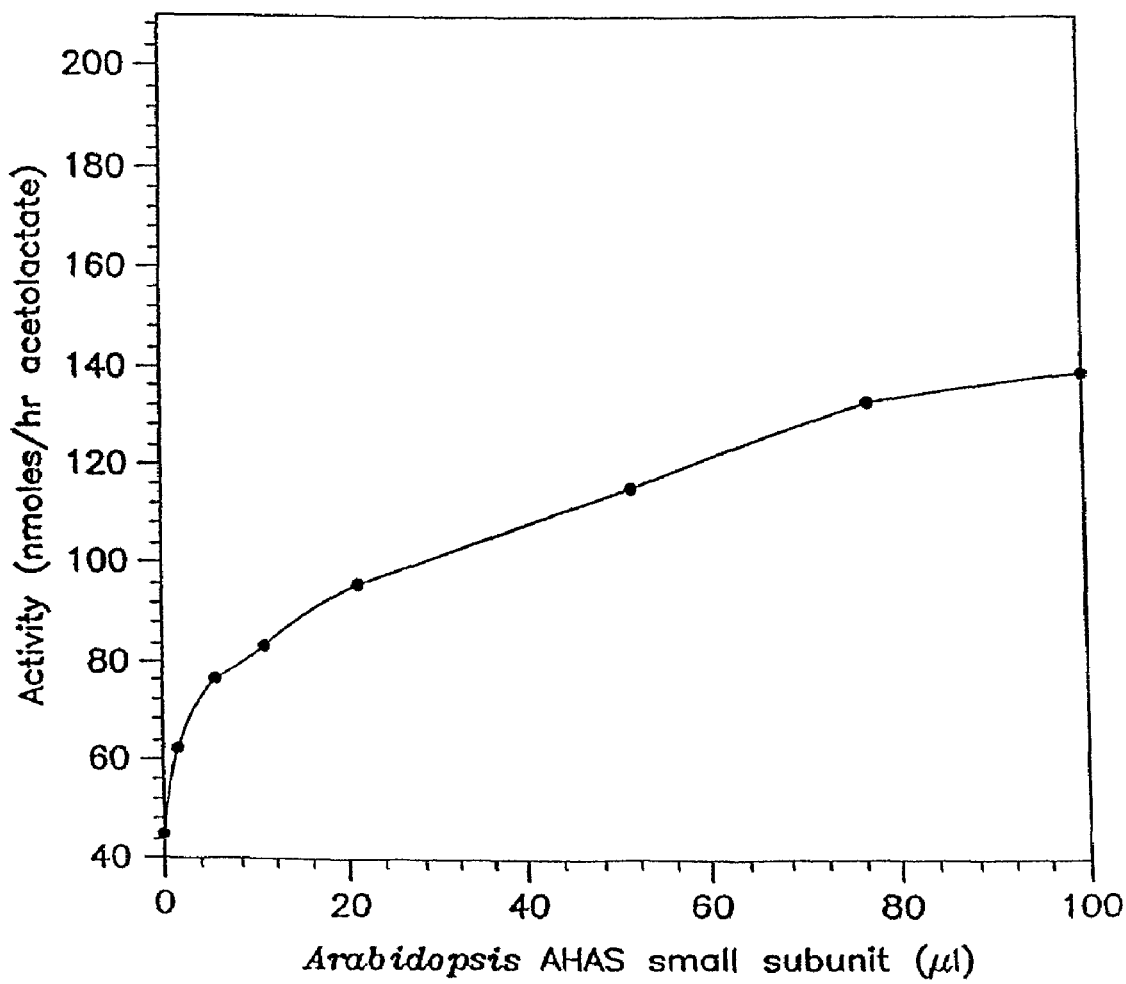
FIG. 8 is a graph showing the activity in vitro of the wild type large subunit protein of the AHAS enzyme in increasing amounts of the *Arabidopsis* small subunit protein.

FIG. 8 shows the activation of the wild type *Arabidopsis* AHAS large subunit by addition of the *Arabidopsis* small subunit protein. AHAS assays were carried out as described above and the results shown in FIG. 8 indicate that small subunit protein enhances the level of enzymatic activity of the catalytic large subunit. The activation of the large subunit protein of AHAS is shown for both the wild type large subunit and a herbicide-resistant mutant of the large subunit.

Figure 9:
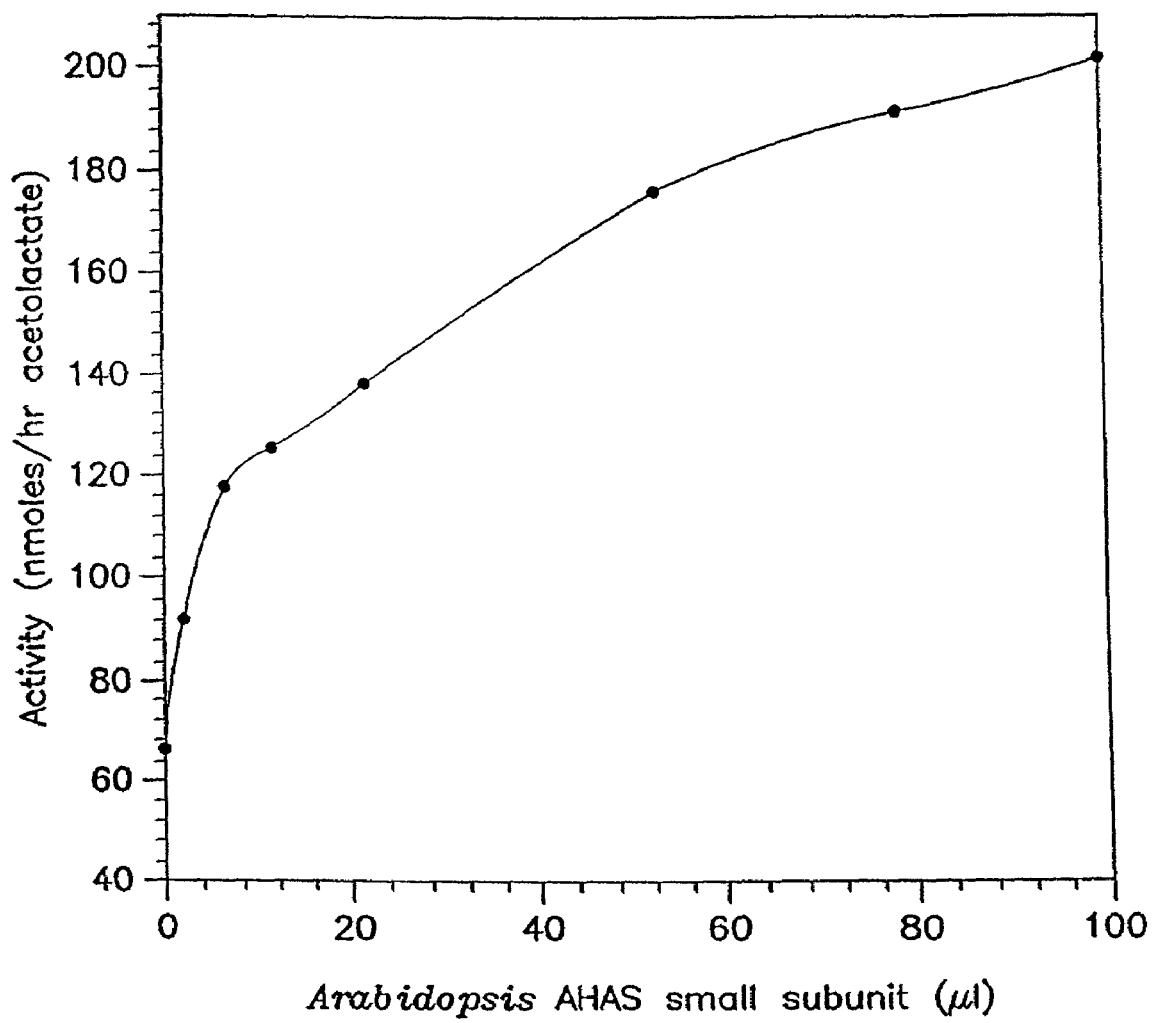
FIG. 9 is a graph showing the in vitro activity of an herbicide resistant mutant (Met124 His) large subunit *Arabidopsis* AHAS protein in the presence of the *Arabidopsis* AHAS small subunit protein.

In another experiment, a herbicide-resistant mutant of the large subunit enzyme (substitution mutation at position 124, methionine substituted by histidine) was used. The results shown in FIG. 9 demonstrate that the enzymatic activity of a herbicide-resistant form of the large subunit is also enhanced.

EXAMPLE 5

Figure 10:
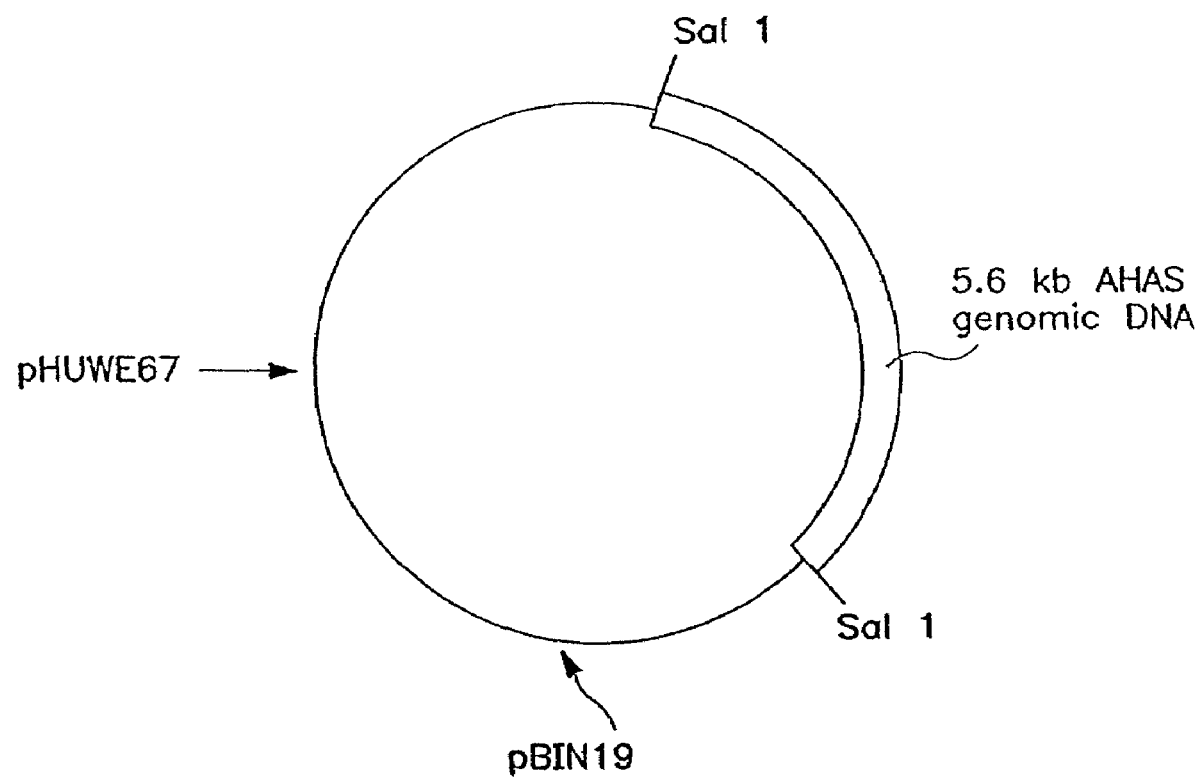
FIG. 10 is a plant transformation vector, pHUWE67 of the invention which contains a 5.6 kb DNA fragment containing the AHAS small subunit genomic DNA.

The plant transformation vector, pHUWE67 illustrated in FIG. 10 containing the *Arabidopsis* AHAS small subunit genomic DNA was constructed as follows. The pUC19 vector shown in FIG. 1 containing the 5.6 kb genomic fragment of the *Arabidopsis* AHAS small subunit gene (pMSg6) was cut with Sal I. The 5.6 kb fragment containing the entire *Arabidopsis* AHAS small subunit gene (see FIG. 2), including the promoter and introns was separated from the vector by agarose gel electrophoresis. The fragment was cut out of the agarose gel and purified using the QIAquick Gel Extraction Kit (Cat. No. 28706) following the procedures provided by the manufacturer. The *Agrobacterium* based transformation vector, pBIN19, was cut with Sal I. The vector was purified by phenol:chloroform extractions. The purified vector was dephosphorylated by treatment with calf intestinal alkaline phosphatase and re-extracted with phenol:chloroform. The vector and genomic insert were ligated and the ligation mix containing the construct was used to transform *E. coli* strain DH5α. *E. coli* was selected on kanamycin plates and plasmids were extracted from transformed *E. coli*. The vector construct was verified by generation of a PCR product and sequencing of the product using the sequencing procedures described in Example 1. The vector designated pHUWE67 (FIG. 10), thus contains a 5.6 kb fragment comprising the AHAS genomic DNA containing the AHAS promoter, an Open Reading Frame (ORF) and 3'-terminator fused with the pBIN19 plasmid. This vector construct is used for *Agrobacterium* based transformation of plants using standard techniques.

The plant transformation vectors illustrated in FIGS. 11A-11E are similarly constructed as vector pHUWE67 above, following standard cloning procedures. In FIG. 11A-11E, the vector may comprise an AHAS small subunit cDNA, fragment, genomic fragment or mutant. In FIG. 11B the vector further comprises an AHAS small subunit promoter operably-linked upstream of the gene insert. In this embodiment, the *Arabidopsis* small subunit gene includes the terminator.

In FIG. 11C the vector construct contains the AHAS small and large subunit genes in tandem, with the large subunit gene downstream from the small subunit gene. Both genes are regulated by the AHAS small subunit promoter which is located upstream from the gene inserts. The AHAS large subunit gene is a herbicide resistant mutant allele.

In FIG. 11D the plant expression vector contains the large and small subunit genes under the control of their own promoters. Transcription termination signal is provided by the AHAS small subunit terminator. The AHAS large subunit gene confers resistant to herbicides such as imidazolinone.

The vector in FIG. 11E is similar to the vector represented in FIG. 11C. In this vector, however, the AHAS large and small subunit genes are reversed in position in the construct. The AHAS large subunit gene in this example is upstream of the small subunit gene. The AHAS large subunit gene is a herbicide resistant mutant allele.

Based on the techniques of present invention and following astringent DNA hybridization techniques, homologous AHAS small subunit gene sequences can be obtained from a variety of plant species, such as rice, maize, wheat, barley, and the like. Therefore, these AHAS small subunit gene sequences are also useful in the present vectors and methods for transforming plants.

The invention claimed is:

1. An isolated DNA molecule comprising nucleotides 1-757 of the nucleotide sequence set forth in SEQ ID NO:3.

2. A plant expression vector comprising a promoter operably linked to a heterologous DNA sequence, said promoter comprising nucleotides 1-757 of the nucleotide sequence set forth in SEQ ID NO:3.

3. The plant expression vector of claim 2, wherein the heterologous DNA sequence encodes an AHAS large subunit protein.

4. A transgenic plant whose genetic complement comprises a plant expression vector comprising a promoter operably linked to a heterologous DNA sequence, said promoter comprising nucleotides 1-757 of the nucleotide sequence set forth in SEQ ID NO:3.

5. A progeny plant of a transgenic plant whose genetic complement comprises a plant expression vector comprising a promoter operably linked to a heterologous DNA sequence, said promoter comprising nucleotides 1-757 of the nucleotide sequence set forth in SEQ ID No:3, wherein said progeny plant comprises said plant expression vector.

6. A transgenic seed of the transgenic plant whose genetic complement comprises a plant expression vector comprising a promoter operably linked to a heterologous DNA sequence, said promoter comprising nucleotides 1-757 of the nucleotide sequence set forth in SEQ ID No:3, wherein said seed comprises said plant expression vector.

7. A method for expressing a heterologous DNA sequence in a plant cell comprising transforming a plant cell with a plant expression vector comprising a promoter operably linked to a heterologous DNA sequence, said promoter comprising nucleotides 1-757 of the nucleotide sequence set forth in SEQ ID NO:3.

8. A transformed plant cell produced by a method comprising transforming a plant cell with a plant expression vector comprising a promoter operably linked to a heterologous DNA sequence, said promoter comprising nucleotides 1-757 of the nucleotide sequence set forth in SEQ ID No:3.

* * * * *

UNITED STATES PATENT AND TRADEMARK OFFICE
CERTIFICATE OF CORRECTION

PATENT NO. : 7,498,429 B2
APPLICATION NO. : 12/027011
DATED : March 3, 2009
INVENTOR(S) : Kakefuda et al.

It is certified that error appears in the above-identified patent and that said Letters Patent is hereby corrected as shown below:

Column 38,

Line 19, "the" should read --a--.

Signed and Sealed this

Second Day of February, 2010

David J. Kappos
*Director of the United States Patent and Trademark Office*

SEQUENCE LISTING

<160> NUMBER OF SEQ ID NOS: 11

<210> SEQ ID NO 1
<211> LENGTH: 1673
<212> TYPE: DNA
<213> ORGANISM: Arabidopsis sp.
<220> FEATURE:
<221> NAME/KEY: CDS
<222> LOCATION: (42)..(1514)
<223> OTHER INFORMATION: Mature Peptide

<400> SEQUENCE: 1

```
gtcttcttca gtagcaaaaa accttcggct tcgtctcgtc a atg gcg gcc att tct      56
                                              Met Ala Ala Ile Ser
                                              1               5 gta agt tct tca cca tct att cgc tgc ttg aga tcg gca tgt tcc gat       104
```

|     |     |     |     |     |     |     |     |     |     |     |     |     |     |     | |
|-----|-----|-----|-----|-----|-----|-----|-----|-----|-----|-----|-----|-----|-----|-----|---|
| Val | Ser | Ser | Ser | Pro | Ser | Ile | Arg | Cys | Leu | Arg | Ser | Ala | Cys | Ser | Asp |
| 10  |     |     |     | 15  |     |     |     | 20  |     |     |     |     |     |     |     |

```
tct tct cct gct ctt gta tcc tcg acg cgt gta tcg ttc ccg gcg aag      152
Ser Ser Pro Ala Leu Val Ser Ser Thr Arg Val Ser Phe Pro Ala Lys
 25          30                  35 att tca tat ctc tcc ggt ata tct tcg cac cgt ggc gat gaa atg ggt      200
Ile Ser Tyr Leu Ser Gly Ile Ser Ser His Arg Gly Asp Glu Met Gly
 40          45                  50 aag aga atg gaa gga ttc gtt aga agc gtc gat ggg aag atc tct gat      248
Lys Arg Met Glu Gly Phe Val Arg Ser Val Asp Gly Lys Ile Ser Asp
 55          60                  65 gcg tct ttc tcc gaa gct tca tct gcg act cca aaa tcg aag gtg agg      296
Ala Ser Phe Ser Glu Ala Ser Ser Ala Thr Pro Lys Ser Lys Val Arg
 70          75                  80              85 aag cac aca att tca gta ttt gtt gga gac gaa agc gga atg att aat      344
Lys His Thr Ile Ser Val Phe Val Gly Asp Glu Ser Gly Met Ile Asn
 90          95                 100 agg att gca gga gtg ttt gca agg aga gga tac aat att gag agt ctt      392
Arg Ile Ala Gly Val Phe Ala Arg Arg Gly Tyr Asn Ile Glu Ser Leu
105         110                 115 gct gtt ggt ctg aac aga gac aag gct cta ttc acc ata gtt gtc tgt      440
Ala Val Gly Leu Asn Arg Asp Lys Ala Leu Phe Thr Ile Val Val Cys
120         125                 130 gga act gaa agg gta ctt cag cag gtc atc gag caa ctc cag aag ctc      488
Gly Thr Glu Arg Val Leu Gln Gln Val Ile Glu Gln Leu Gln Lys Leu
135         140                 145 gtt aat gtt cta aag gtt gaa gat atc tca agt gag ccg caa gtg gag      536
Val Asn Val Leu Lys Val Glu Asp Ile Ser Ser Glu Pro Gln Val Glu
150         155                 160             165 cgt gag ctg atg ctt gta aaa gtg aat gca cat cca gaa tcc agg gca      584
Arg Glu Leu Met Leu Val Lys Val Asn Ala His Pro Glu Ser Arg Ala
170         175                 180 gag atc atg tgg cta gtt gac aca ttc aga gca aga gtt gta gat ata      632
Glu Ile Met Trp Leu Val Asp Thr Phe Arg Ala Arg Val Val Asp Ile
185         190                 195 gcg gaa cat gca ttg act atc gag gta act gga gat cct gga aaa atg      680
Ala Glu His Ala Leu Thr Ile Glu Val Thr Gly Asp Pro Gly Lys Met
200         205                 210 att gct gta gaa aga aat ttg aaa aag ttt cag atc aga gag att gta      728
Ile Ala Val Glu Arg Asn Leu Lys Lys Phe Gln Ile Arg Glu Ile Val
215         220                 225 agg aca gga aag ata gca ctg aga agg gaa aag atg ggt gca act gct      776
Arg Thr Gly Lys Ile Ala Leu Arg Arg Glu Lys Met Gly Ala Thr Ala
230         235                 240             245 cca ttt tgg cga ttt tca gca gca tcc tat cca gat ctc aag gag caa      824
Pro Phe Trp Arg Phe Ser Ala Ala Ser Tyr Pro Asp Leu Lys Glu Gln
250         255                 260 gcg cct gtt agt gtt ctt cga agt agc aaa aaa gga gcc att gtc cct      872
Ala Pro Val Ser Val Leu Arg Ser Ser Lys Lys Gly Ala Ile Val Pro
265         270                 275 caa aag gaa aca tca gca ggg gga gat gtt tat ccc gtt gag cca ttt      920
Gln Lys Glu Thr Ser Ala Gly Gly Asp Val Tyr Pro Val Glu Pro Phe
280         285                 290 ttt gac ccc aag gta cat cgt att ctc gac gct cac tgg gga ctt ctc      968
Phe Asp Pro Lys Val His Arg Ile Leu Asp Ala His Trp Gly Leu Leu
295         300                 305 act gac gaa gat acg agt gga cta cgg tcg cat act cta tca ttg ctt     1016
Thr Asp Glu Asp Thr Ser Gly Leu Arg Ser His Thr Leu Ser Leu Leu
310         315                 320             325
```

-continued

| | |
|---|---|
| gta aat gat att cca gga gtt ctt aat att gtg act ggt gtt ttc gct<br>Val Asn Asp Ile Pro Gly Val Leu Asn Ile Val Thr Gly Val Phe Ala<br>330                      335                      340 | 1064 |
| cga agg gga tac aat atc cag agc ttg gcc gta gga cat gct gaa acc<br>Arg Arg Gly Tyr Asn Ile Gln Ser Leu Ala Val Gly His Ala Glu Thr<br>345                      350                      355 | 1112 |
| aag ggc att tca cgc att aca aca gtt ata cct gca aca gat gaa tcg<br>Lys Gly Ile Ser Arg Ile Thr Thr Val Ile Pro Ala Thr Asp Glu Ser<br>360                      365                      370 | 1160 |
| gtc agc aaa ttg gtg cag caa ctt tac aaa ctc gta gat gtg cat gag<br>Val Ser Lys Leu Val Gln Gln Leu Tyr Lys Leu Val Asp Val His Glu<br>375                      380                      385 | 1208 |
| gtc cat gat ctt act cat ttg cca ttt tct gaa aga gaa ctg atg ctg<br>Val His Asp Leu Thr His Leu Pro Phe Ser Glu Arg Glu Leu Met Leu<br>390                      395                      400                      405 | 1256 |
| att aag att gcc gtg aac gct gct gct aga aga gat gtc ctg gac att<br>Ile Lys Ile Ala Val Asn Ala Ala Ala Arg Arg Asp Val Leu Asp Ile<br>410                      415                      420 | 1304 |
| gct agt att ttc agg gct aaa gct gtt gac gta tct gat cac aca att<br>Ala Ser Ile Phe Arg Ala Lys Ala Val Asp Val Ser Asp His Thr Ile<br>425                      430                      435 | 1352 |
| act ttg cag ctt act ggg gat cta gac aag atg gtt gca ctg caa agg<br>Thr Leu Gln Leu Thr Gly Asp Leu Asp Lys Met Val Ala Leu Gln Arg<br>440                      445                      450 | 1400 |
| tta ttg gag ccc tat ggt ata tgt gag gtt gca aga acc ggt cgt gtg<br>Leu Leu Glu Pro Tyr Gly Ile Cys Glu Val Ala Arg Thr Gly Arg Val<br>455                      460                      465 | 1448 |
| gca ttg gct cgt gaa tcg gga gtg gac tcc aag tac ctt cgt gga tac<br>Ala Leu Ala Arg Glu Ser Gly Val Asp Ser Lys Tyr Leu Arg Gly Tyr<br>470                      475                      480                      485 | 1496 |
| tcc ttt ctt tta aca ggc taaaccgttg cagagtgcat ccatcgaaca<br>Ser Phe Leu Leu Thr Gly<br>490 | 1544 |
| tcagaaactt tggaaggtaa agtttcatt acacagtcta tgaacctcaa agacagacag | 1604 |
| agagactgcg tcgatatatg tttgtgactt tgtttatgaa acaattagct gattttgggc | 1664 |
| ttcatttcg | 1673 |

<210> SEQ ID NO 2
<211> LENGTH: 491
<212> TYPE: PRT
<213> ORGANISM: Arabidopsis sp.

<400> SEQUENCE: 2

Met Ala Ala Ile Ser Val Ser Ser Pro Ser Ile Arg Cys Leu Arg
1                 5                    10                   15

Ser Ala Cys Ser Asp Ser Ser Pro Ala Leu Val Ser Ser Thr Arg Val
20                      25                    30

Ser Phe Pro Ala Lys Ile Ser Tyr Leu Ser Gly Ile Ser Ser His Arg
35                      40                    45

Gly Asp Glu Met Gly Lys Arg Met Glu Gly Phe Val Arg Ser Val Asp
50                      55                    60

Gly Lys Ile Ser Asp Ala Ser Phe Ser Glu Ala Ser Ser Ala Thr Pro
65                 70                    75                    80

Lys Ser Lys Val Arg Lys His Thr Ile Ser Val Phe Val Gly Asp Glu
85                      90                    95

Ser Gly Met Ile Asn Arg Ile Ala Gly Val Phe Ala Arg Arg Gly Tyr
100                    105                  110

```
Asn Ile Glu Ser Leu Ala Val Gly Leu Asn Arg Asp Lys Ala Leu Phe
115                 120                 125

Thr Ile Val Val Cys Gly Thr Glu Arg Val Leu Gln Gln Val Ile Glu
130                 135                 140

Gln Leu Gln Lys Leu Val Asn Val Leu Lys Val Glu Asp Ile Ser Ser
145                 150                 155                 160

Glu Pro Gln Val Glu Arg Glu Leu Met Leu Val Lys Val Asn Ala His
        165                 170                 175

Pro Glu Ser Arg Ala Glu Ile Met Trp Leu Val Asp Thr Phe Arg Ala
180                 185                 190

Arg Val Val Asp Ile Ala Glu His Ala Leu Thr Ile Glu Val Thr Gly
195                 200                 205

Asp Pro Gly Lys Met Ile Ala Val Glu Arg Asn Leu Lys Lys Phe Gln
210                 215                 220

Ile Arg Glu Ile Val Arg Thr Gly Lys Ile Ala Leu Arg Arg Glu Lys
225                 230                 235                 240

Met Gly Ala Thr Ala Pro Phe Trp Arg Phe Ser Ala Ala Ser Tyr Pro
245                 250                 255

Asp Leu Lys Glu Gln Ala Pro Val Ser Val Leu Arg Ser Ser Lys Lys
260                 265                 270

Gly Ala Ile Val Pro Gln Lys Glu Thr Ser Ala Gly Gly Asp Val Tyr
275                 280                 285

Pro Val Glu Pro Phe Phe Asp Pro Lys Val His Arg Ile Leu Asp Ala
290                 295                 300

His Trp Gly Leu Leu Thr Asp Glu Asp Thr Ser Gly Leu Arg Ser His
305                 310                 315                 320

Thr Leu Ser Leu Leu Val Asn Asp Ile Pro Gly Val Leu Asn Ile Val
325                 330                 335

Thr Gly Val Phe Ala Arg Arg Gly Tyr Asn Ile Gln Ser Leu Ala Val
340                 345                 350

Gly His Ala Glu Thr Lys Gly Ile Ser Arg Ile Thr Thr Val Ile Pro
355                 360                 365

Ala Thr Asp Glu Ser Val Ser Lys Leu Val Gln Gln Leu Tyr Lys Leu
370                 375                 380

Val Asp Val His Glu Val His Asp Leu Thr His Leu Pro Phe Ser Glu
385                 390                 395                 400

Arg Glu Leu Met Leu Ile Lys Ile Ala Val Asn Ala Ala Ala Arg Arg
405                 410                 415

Asp Val Leu Asp Ile Ala Ser Ile Phe Arg Ala Lys Ala Val Asp Val
420                 425                 430

Ser Asp His Thr Ile Thr Leu Gln Leu Thr Gly Asp Leu Asp Lys Met
435                 440                 445

Val Ala Leu Gln Arg Leu Leu Glu Pro Tyr Gly Ile Cys Glu Val Ala
450                 455                 460

Arg Thr Gly Arg Val Ala Leu Ala Arg Glu Ser Gly Val Asp Ser Lys
465                 470                 475                 480

Tyr Leu Arg Gly Tyr Ser Phe Leu Leu Thr Gly
485                 490

<210> SEQ ID NO 3
<211> LENGTH: 4895
<212> TYPE: DNA
<213> ORGANISM: Arabidopsis sp.
<220> FEATURE:
<221> NAME/KEY: promoter
```

```
<222> LOCATION: (1)..(757)
<223> OTHER INFORMATION: Promoter Region
<220> FEATURE:
<221> NAME/KEY: misc_feature
<222> LOCATION: (717)
<223> OTHER INFORMATION: Transcriptional Starting Point
<220> FEATURE:
<221> NAME/KEY: misc_signal
<222> LOCATION: (758)..(760)
<223> OTHER INFORMATION: Start Codon
<220> FEATURE:
<221> NAME/KEY: misc_signal
<222> LOCATION: (4737)..(4739)
<223> OTHER INFORMATION: Stop Codon
<220> FEATURE:
<223> OTHER INFORMATION: n at position 694 can be a, c, g, or t

<400> SEQUENCE: 3
tcgcatattg ttccggcgag gatcatgtga agcttgacgc gtgaattgac gactaagcgt      60
acgacgaagc gatccagttg agaattgtct cgagattcct cgttttagct gtcccactac     120
attcgccatg atttcgaaat ctctttctct tcttctctct ttcgtcttct tctgcgaaaa     180
aatcgaatgg ataatcacat tttcttttc tcgagaaaat tgatctggtg attatgtgag      240
atccgtctct agcgcgttgc ttatcgagaa ataattaatt ttaatttgac gggtgaagat     300
attattggcg acgtctgttt ccgattgact ttgatttgac ttttcctttc aatcattatt     360
tggcgagtcc cgcgtaaata tggactcttc ttgattgtcc cactttttc ggtggcttta      420 ccggatttaa aatcatttc ttttcctaaa ttatgaattt accctaaac ttctcataat       480 tacaattagt tccgacgaac ccaagatact ttttagcaaa attaggaaaa tagttgactc     540
gaaaaggttg ttataacgtg gagctgacgt gttggtctta tctactcgaa gccttttggg     600
cttttcttaa agccattgat ttctaaggtc gtcaacaacc gaaccggacc ggacggtttg     660
accggtctaa ccaacatata tacgttcttt ttcnacttgc cgtttcgtcg tcgtcagtct     720
tcttcagtag caaaaaacct tcggcttcgt ctcgtcaatg gcggccattt ctgtaagttc     780
ttcaccatct attcgctgct tgagatcggc atgttccgat tcttctcctg ctcttgtatc     840
ctcgacgcgt gtatcgttcc cggcgaagat ttcatatctc tccggtatat cttcgcaccg     900
tggcgatgaa atgggtaaga aatggaagg attcgttaga agcgtcgatg ggaagatctc     960
tgatgcgtct ttctccgaag cttcatctgc gactccaaaa tcgaagcgac tgtgaataat    1020
atttgcttaa agtcgtttcc ttttggcctt tgctttgatt gattctttgt gcattaaaat    1080
cagggtgagg aagcacacaa tttcagtatt tgttggagac gaaagcggaa tgattaatag    1140
gattgcagga gtgtttgcaa ggagaggata caatattgag agtcttgctg ttggtctgaa    1200
cagagacaag gctctattca ccatagttgt ctgtggaact gaaagggtac ttcagcaggt    1260
catcgagcaa ctccagaagc tcgttaatgt tctaaaggtt gttcttttgt tagatcgcac    1320
ttattagttt ctgcatgact atagtttcat tcgcaccaac tttacgcatc agccaatttg    1380
cttattcatt atttgaagat tagatttgcg atttcctttt ccattctctt cattgacttg    1440
gacatgaatt aggttgaaga tatctcaagt gagccgcaag tggagcgtga gctgatgctt    1500
gtaaaagtga atgcacatcc agaatccagg gcagaggtac tattccttgc ctatgggaaa    1560
ttagagttta ctgtacttgc tggttgcttc tgatttaggg cagaggtggt gttagttttc    1620
tctctaaatt tgattaagct tctgtttaa tgaattcaca gatcatgtgg ctagttgaca     1680
cattcagagc aagagttgta gatatagcgg aacatgcatt gactatcgag gtacatctac    1740
ttattatgat ttgtgttggt cttgatattt gtttcgcact gtagcctgtg ggtttcaaga    1800
```

```
cttctgtttg aacatcttac taatcgttgg aagacatcag aaatattatg gagggatcat    1860
tttaactttt atatctatta gttggatttt cgttgccttt tgaaactgat gatgatccac    1920
atgcaggact ctattatagg atgtgtatta aagtttattt gaaacttttg gtgcaacttc    1980
ttgaatttaa tataacgaga aagttattca acagtgtgct acctttgatt accctatgct    2040
tataatctgt attctgagtt gtattgcctg tgcaaatttc tgtgggaatg ctcagtgttc    2100
acttttgaaa gttagagaag cataacctta aatatattgt tcttttacc ttgattatga     2160
gaaagtggag taaagaaag ggtgtctctg atttacctat tttagctctt tagtaatcat     2220
ttttaagcta ttttgcaggt aactggagat cctggaaaaa tgattgctgt agaaagaaat    2280
ttgaaaaagt ttcagatcag agagattgta aggacaggaa aggtagtgta tgtttggaat    2340
tactagattt tatggctttt gaatatcatc tagtttgtgc tatctaatgt atgtatgtag    2400
tagttacatc tttgagtgga cacaaaggca tagatctcag ggactttcac taatttaggg    2460
aaaatggaat gacattttg gataacagat agcactgaga agggaaaaga tgggtgcaac    2520
tgctccattt tggcgatttt cagcagcatc ctatccagat ctcaaggagc aagcgcctgt    2580
tagtgttctt cgaagtagca aaaaggagc cattgtccct caaaggaaa catcagcagg     2640
ggtgtgtgct tctctgctcc ttagattgtt taacttcagc ttgaagttcc tcactttcct    2700
ttcaaaaaat ttggttgcat aaattatagt aggtttggct atttgataaa gttaaacagc    2760
aactatagat gcctgtgttt ttttccctct atgtggtggc tgcctggaat caacatttga    2820
agcatgccct tttttgtttt tctccctggc tgcactgaag gatttccgag tttgctaatt    2880
tttaaaagtt atcttatctt tttaaatgta gggagatgtt tatcccgttg agccattttt    2940
tgaccccaag gtacatcgta ttctcgacgc tcactgggga cttctcactg acgaagatgt    3000
aagagagttc tttgctatat atctaacttc gtgccatgaa tttgctaaaa agcaatatga    3060
aaaattcaga ttgtggtttg cattacacga gttacacttg tttttccatt caagccgtct    3120
ggcataatca attctgttaa tatagttaca taaatgataa atcaattgag tgttagattt    3180
ggagactgta tgtatttact tacaaagcag acattgaaag agttgggtt ttctttaagc     3240
tatttcgttt tatttatcac agttattctt ttttgatctt tcagacgagt ggactacggt    3300
cgcatactct atcattgctt gtaaatgata ttccaggagt tcttaatatt gtgactggtg    3360
ttttcgctcg aaggggatac aatatccagg catagtcctt atctctctca tacacgcaca    3420
cacagtgtgc ttaggtttac tgacacactg aaagatctcc tttcttttag agcttggccg    3480
taggacatgc tgaaaccaag ggcatttcac gcattacaac agttataccг gcaacagatg    3540
aatcggtcag caaattggtg cagcaacttt acaaactcgt agatgtgcat gaggtgggat    3600
taccaaaagc tactgtcttt cttatatatt taacagtttg aatgtctttg atggccctat    3660
cattcctttg ctgtcttaga cctttttggct ttttttaaaa cgtagattag aggaagagtt    3720
tctgctaaat ctttctggac tttcctatat catttcctgg tcttgtctgt ttactcgaat    3780
gagacctctt gttccagaaa gtcaaactgt acaggcttga tgaaaataat tctgaacatg    3840
atttgccgca actttccaag ctgttattaa ctttgtgagg attttctgca ggtccatgat    3900
cttactcatt tgccatttc tgaaagagaa ctgatgctga ttaagattgc cgtgaacgct     3960
gctgctagaa gagatgtcct ggacattgct agtatttca gggctaaagc tgttgacgta     4020
tctgatcaca caattacttt gcaggtaaaa tacatttctc ataaatggga ttttatgta     4080
gctgttattg catctcagat gagaaatcct ttcaattgga gatcttcaaa gtttcacgtc    4140
tttccatagg tcttcaactt gtttgacata atcagagttc cgtttgaaaa aaatatatga    4200
```

-continued

```
agctgacttg gattttccat cttaatctct ttttttttgct tttgtgtttt ggatttgtgt    4260
gctgaaattt gttggctgtg ggtatagctt actggggatc tagacaagat ggttgcactg    4320
caaaggttat tggagcccta tggtatatgt gaggtttgtt tcgcaatcta ctttcatctc    4380
ttagtgaatg cataaccccg tgaattctta tttcttataa tgctacccca attgctccgg    4440
ataaagtccc aaaatttagt tgtagtcttt acgacttaga aacagagtag tgaacatcta    4500
actctctggt aaaatcaata accaaagctg gacctagtta catgaatctt cttctggttg    4560
tgtgtagaac aagaataagc ttgacaagcc atgactactt tcagattatg catcgtgttg    4620
acgcttatta tgaacaatca atcacacagg ttgcaagaac cggtcgtgtg gcattggctc    4680
gtgaatcggg agtggactcc aagtaccttc gtggatactc ctttctttta acaggctaaa    4740
ccgttgcaga gtgcatccat cgaacatcag aaactttgga aggtaaaagt ttcattacac    4800
agtctatgaa cctcaaagac agacagagag actgcgtcga tatatgtttg tgactttgtt    4860
tatgaaacaa ttagctgatt ttgggcttca tttcg                               4895
```

```
<210> SEQ ID NO 4
<211> LENGTH: 22
<212> TYPE: DNA
<213> ORGANISM: Artificial Sequence
<220> FEATURE:
<223> OTHER INFORMATION: Description of Artificial Sequence:Primer made
      from cDNA sequence
<220> FEATURE:
<221> NAME/KEY: misc_feature
<222> LOCATION: (1)..(22)
<223> OTHER INFORMATION: DNA primer

<400> SEQUENCE: 4
cagagatcat gtggctagtt ga                                              22

<210> SEQ ID NO 5
<211> LENGTH: 22
<212> TYPE: DNA
<213> ORGANISM: Artificial Sequence
<220> FEATURE:
<223> OTHER INFORMATION: Description of Artificial Sequence:Primer made
      from cDNA sequence
<220> FEATURE:
<221> NAME/KEY: misc_feature
<222> LOCATION: (1)..(22)
<223> OTHER INFORMATION: DNA primer

<400> SEQUENCE: 5
gagcgtcgag aatacgatgt ac                                              22

<210> SEQ ID NO 6
<211> LENGTH: 6
<212> TYPE: PRT
<213> ORGANISM: Artificial Sequence
<220> FEATURE:
<223> OTHER INFORMATION: Description of Artificial Sequence:Thrombin
      cleavage site

<400> SEQUENCE: 6

Leu Val Pro Arg Gly Ser
1               5

<210> SEQ ID NO 7
<211> LENGTH: 6
<212> TYPE: PRT
<213> ORGANISM: Arabidopsis sp.
<220> FEATURE:
```

```
<221> NAME/KEY: PEPTIDE
<222> LOCATION: (1)..(6)
<223> OTHER INFORMATION: N-terminal of AHAS small subunit peptide of
      pHUWE82
<220> FEATURE:
<221> NAME/KEY: SITE
<222> LOCATION: (1)..(2)
<223> OTHER INFORMATION: Thrombin cleavage site

<400> SEQUENCE: 7

Gly Ser Ile Ser Val Ser
1               5

<210> SEQ ID NO 8
<211> LENGTH: 6
<212> TYPE: PRT
<213> ORGANISM: Arabidopsis sp.
<220> FEATURE:
<221> NAME/KEY: PEPTIDE
<222> LOCATION: (1)..(6)
<223> OTHER INFORMATION: N-terminal of AHAS small subunit peptide of
      pHUWE83
<220> FEATURE:
<221> NAME/KEY: SITE
<222> LOCATION: (1)..(2)
<223> OTHER INFORMATION: Thrombin cleavage site

<400> SEQUENCE: 8

Gly Ser Met Ile Asn Arg
1               5

<210> SEQ ID NO 9
<211> LENGTH: 8
<212> TYPE: PRT
<213> ORGANISM: Arabidopsis sp.
<220> FEATURE:
<221> NAME/KEY: PEPTIDE
<222> LOCATION: (1)..(8)
<223> OTHER INFORMATION: N-terminal sequence of AHAS small subunit
      peptide of plasmid F1
<220> FEATURE:
<221> NAME/KEY: SITE
<222> LOCATION: (1)..(2)
<223> OTHER INFORMATION: Thrombin cleavage site

<400> SEQUENCE: 9

Gly Ser Pro Lys Ile Ala Leu Arg
1               5

<210> SEQ ID NO 10
<211> LENGTH: 7
<212> TYPE: PRT
<213> ORGANISM: Arabidopsis sp.
<220> FEATURE:
<221> NAME/KEY: PEPTIDE
<222> LOCATION: (1)..(7)
<223> OTHER INFORMATION: N-terminal sequence of AHAS small subunit
      peptide of plasmid F2
<220> FEATURE:
<221> NAME/KEY: SITE
<222> LOCATION: (1)..(2)
<223> OTHER INFORMATION: Thrombin cleavage site

<400> SEQUENCE: 10

Gly Ser Leu Asp Ala His Trp
1               5

<210> SEQ ID NO 11
<211> LENGTH: 7
<212> TYPE: PRT
<213> ORGANISM: Arabidopsis sp.
```

```
-continued
<220> FEATURE:
<221> NAME/KEY: PEPTIDE
<222> LOCATION: (1)..(7)
<223> OTHER INFORMATION: N-terminal  of AHAS small subunit peptide from
      plasmid F3
<220> FEATURE:
<221> NAME/KEY: SITE
<222> LOCATION: (1)..(2)
<223> OTHER INFORMATION: Thrombin cleavage site

<400> SEQUENCE: 11

Gly Ser Val Glu Pro Phe Phe
1               5
```